(12) United States Patent
Kawashima et al.

(10) Patent No.: US 7,816,511 B2
(45) Date of Patent: Oct. 19, 2010

(54) REMEDIES FOR HEART FAILURE

(75) Inventors: Kayoko Kawashima, Takatsuki (JP); Naruto Katsuragi, Ibaraki (JP); Keijiro Sugimura, Ibaraki (JP); Mayumi Furuya, Osaka (JP); Ryuichi Morishita, Osaka (JP)

(73) Assignee: Asubio Pharma Co., Ltd., Tokyo (JP)

( * ) Notice: Subject to any disclaimer, the term of this patent is extended or adjusted under 35 U.S.C. 154(b) by 0 days.

(21) Appl. No.: 10/383,241

(22) Filed: Jul. 16, 2003

(65) Prior Publication Data
US 2004/0029827 A1 Feb. 12, 2004

Related U.S. Application Data

(63) Continuation of application No. PCT/JP01/07787, filed on Sep. 7, 2001.

(30) Foreign Application Priority Data

Sep. 8, 2000 (JP) .............................. 2000-273644

(51) Int. Cl.
C07H 21/04 (2006.01)
A01N 43/04 (2006.01)
A61K 31/70 (2006.01)

(52) U.S. Cl. ........................................ 536/24.5; 514/44
(58) Field of Classification Search ................ 536/24.5; 514/44
See application file for complete search history.

(56) References Cited

U.S. PATENT DOCUMENTS

| 5,756,664 | A  | * | 5/1998 | Amann et al. ................ 530/326 |
| 6,228,642 | B1 | * | 5/2001 | Baker et al. .................. 435/375 |
| 6,271,030 | B1 | * | 8/2001 | Monia et al. ................. 435/375 |
| 6,559,294 | B1 | * | 5/2003 | Griffais et al. ............. 536/23.1 |
| 6,709,855 | B1 | * | 3/2004 | Stanton et al. ........... 435/283.1 |

FOREIGN PATENT DOCUMENTS

| EP | 0 490 818 | 6/1992 |
| EP | 1 347 051 A | 9/2003 |
| HU | P9103662 | 1/1993 |
| WO | WO 00/35473 | 6/2000 |
| WO | WO 02/060317 A | 8/2002 |

OTHER PUBLICATIONS

Webpage: familydoctor.org, (familydoctor.org/119.xml): viewed Jan. 16, 2005, posted Sep. 2000 and updated Nov. 2001.*
Webster's II New Riverside Dictionary. 1994 The Riverside Publishing Company. pp. 933 and 944.*
Carninci et al. Genbank Locus: AV168299: *Mus musculus* head C57BL/6J cDNA. EST: Jul. 6, 1999.*
Opalinska et al. Nature Reviews Drug Discovery, 2002, vol. 1, p. 503-514.*
Bennett et al. (Biochimica et Biophysica 1489, 1999, 19-30).*
Ex parte Toyoko Kusama, Koichi Kadowaki, and Tetsuya Nomura, Appeal 2009-001929.*
In re Gleave CAFC 2008-1453.*
Uhlmann et al. (Chemical Review 90-543-584, 1990).*
S.E. Johnatty, J.R.B. Dyck, L.H. Michael, E.N. Olson , M. Abdellatif, "Identification of Genes Regulated During Mechanical Load-Induced Cardiac Hypertrophy", J. Mol. Cell. Cardiology, May 2000, vol. 32, Issue No. 5, pp. 805-515.
L.W. Stanton, L.J. Garrard, D. Damm, B.L. Garrick, A. Lam, A.M. Kapoun, Q. Zheng, A.A. Protter, G.F. Schreiner, R.T. White, "Altered Patterns of Gene Expression in Response to Myocardial Infarction", Circulation Research, (2000), vol. 86, Issue No. 9, pp. 939-945.
S. Takeshita, R. Kikuno, K-I Tezuka, E. Amann, "Osteoblast-specific factor 2: cloning of a putative bone adhesion protein with homolgy with the insect protein fasciclin I", Biochem. J., (1993), vol. 294, pp. 271-278.
Haertel-Wiesmann, Marion et al.: "Regulation of cyclooxygenase-2 and periostin by Wnt-3 in mouse mammary epithelial cells" Journal of Biological Chemistry (2000), 275(41), 32046-32051.
Chemical Abstracts Service Database Accession No. 77:83708 CA XP002267760: Schaumann, E. et al.: "Clinical-pharmacological studies with a new orally active adenosine derivative" Arzneimittel-Forschung (1972), 22(4), 783-90.
Spalding, M.B. et al.: "The hemodynamic effects of adenosine infusion after experimental right heart infarct in young swine" Journal of Cardiovascular Pharmacology, vol. 35, No. 1, Jan. 2000, pp. 93-99.
Kitakaze, Masafumi et al.: "Adenosine therapy: a new approach to chronic heart failure" Expert Opinion on Investigational Drugs (2000), 9(11), 2519-2535.
Nanto et al., "Intracoronary Administration of Adenosine Triphosphate Increases Myocardial Adenosine Levels and Coronary Blood Flow in Man", Japanese Circulation Journal, vol. 61, p. 836-842, 1997.
Fischer, et al., "Identification of Potent, Selective $P_{2\gamma}$-Purinoceptor Agonists: Structure-Activity Relationships for 2-Thioehter Derivatives of Adenosine 5'-Triphosphate", J. Med. Chem., vol. 36, No. 24, p. 3937-3946, 1993.
Ducy, et al. (1997) "OSF2/CBFA1: A Transcriptional Activator of Osteoblast Differentiation." Cell 89: 747-754.

* cited by examiner

*Primary Examiner*—Brian Whiteman
(74) *Attorney, Agent, or Firm*—Hunton & Williams LLP

(57) ABSTRACT

The present invention provides methods for screening drugs inhibiting the expression of OSF-2 gene or the production or function of the protein encoded thereby and therapeutic agents for heart failure having such effects. Useful methods for diagnosing heart failure can be provided by monitoring the expression or variation of said gene or the production of the protein encoded thereby. The present invention also provides transgenic animals with forced expression of OSF-2 gene and methods for studying changes in gene expression or protein production or the functions of various genes or proteins with the progress of the pathology of heart failure using them and novel therapeutic agents for heart failure.

14 Claims, 3 Drawing Sheets

REMEDIES FOR HEART FAILURE

This application claims benefit of priority and is a continuation application of PCT International Application No. PCT/JP01/07787, filed on Sep. 7, 2001, which claims the benefit of priority of Japanese Patent Application No. 273644/2000, filed Sep. 8, 2000. These documents are incorporated by reference herein in their entirety.

FIELD OF THE INVENTION

The present invention relates to prophylactic or therapeutic agents for heart failure, methods for screening substances suitable as active ingredients of the prophylactic or therapeutic agents, diagnostic agents or diagnostic kits for heart failure and non-human transgenic animals, etc.

BACKGROUND OF THE INVENTION

Chronic heart failure is a disease in which the heart cannot maintain an adequate cardiac output to various organs due to reduced myocardial contractility, and conventional therapies therefor include the use of cardiac stimulants that increase myocardial contractility such as digitalis and xanthine drugs. However, these drugs have been shown to adversely affect vital prognosis as a result of increased consumption of myocardial energy during prolonged administration. Recently, therapies with β-blockers or ACE inhibitors have prevailed that reduce overload on the heart caused by over activation of the sympathetic nervous system or the renin-angiotensin system in patients with heart failure. However, long-term vital prognosis of patients with heart failure is still poor and it would be desirable to develop a drug for treating heart failure based on a new mechanism.

SUMMARY OF THE INVENTION

Thus, the present invention aims to provide a novel prophylactic or therapeutic agent for heart failure or the like based on a different mechanism from existing ones. More specifically, the present invention aims to provide a drug for preventing or treating heart failure by inhibiting aggravation of heart disease induced by OSF-2 gene or protein, a method for screening a substance suitable as an active ingredient of said drug, a useful diagnostic method for heart failure comprising monitoring the expression or variation of OSF-2 gene or the production of OSF-2 protein and a diagnostic agent or a diagnostic kit used for diagnosing heart failure, and a non-human transgenic animal capable of forced expression of OSF-2 gene.

On the hypothesis that the expression of various genes or proteins in the heart varies with the progress of the pathology of heart failure and that these variations are closely related to the pathology of heart failure, we searched for genes whose expression level varies with the progress of the pathology of heart failure using appropriate heart failure models. As a result, we found that the expression of OSF-2 gene known as a gene specifically expressed in osteoblasts increases with the progress of heart failure. Further studies revealed that said gene or protein influences aggravation of heart failure, which led us to accomplish the present invention on the basis that any drug inhibiting the expression or function thereof should be a novel therapy for heart failure.

In the development of therapeutic agents for heart failure, various pathologic models are used, and especially in initial screening, rat models are often used because of the convenience of preparation of the models or easy analysis. In other words, rat models are accepted as models reflecting human pathologies though they individually have limitations.

Known pathologic model rats of heart failure include aortostenotic rats, arteriovenous shunt rats, coronary artery ligature rats, spontaneously hypertensive rats (SHR), Dahl salt-sensitive rats, etc. Dahl rats are Sprague-Dawley strain rats separated into salt-sensitive rats (Dahl-S) susceptible to hypertension and salt-resistant rats (Dahl-R) resistant to hypertension at the third generation of crossing while being raised on an 8% high salt diet. Kihara et al. of Kyoto University showed that Dahl-S rats raised on an 8% high salt diet from 6-weeks of age developed compensatory left ventricular hypertrophy, then left ventricular dilatation accompanied by contraction failure, i.e. uncompensated heart failure, and finally died of pulmonary congestion (Am. J. Physiol., 267, H2471-2482 (1994)). We selected Dahl salt-sensitive rats as pathologic models of heart failure because they can be prepared without any special techniques and can shortly develop heart failure and also can be clearly separated between compensatory hypertrophy stage and uncompensated heart failure stage in each individual and show a similar onset process to that of human hypertensive heart failure.

Known methods for detecting a gene with varied expression in pathological conditions include subtraction, differential display, dot blotting and microarray techniques. In the present invention, subtraction technique was used to succeed in detecting genes whose expression varies at the transition from cardiac hypertrophy stage to heart failure stage. They included a novel rat OSF-2 gene shown to have a high homology to the mouse OSF-2 gene that had been reported as an osteoblast-specific factor.

OSF-2 gene was isolated and identified as a gene specifically expressed in the mouse osteoblast cell line MC3T3-E1 (Biochem. J. 294, 271-278, 1993, JPA 1993/268982), and reported to have adhesion-promoting activity in osteoblast cells (J. Bone. Miner. Res. 14 1239-1249, 1999). An increased expression of OSF-2 gene has been reported in an analysis by differential display in rabbit abdominal aorta lesion models (J. Hum. Genet. 43, 9-13, 1998). Recent reports also showed that the expression of 30 or more genes including OSF-2 varied at cardiac hypertrophy stage in experiments using mice (J. Mol. Cell. Cardiol., 32, 805-815, 2000) and that the expression of 200 or more genes including OSF-2 varied in a rat myocardial infarct model (Circ. Res., 86, 939-945, 2000).

However, it has not been known until now that further expression is induced with the progress to the pathology of heart failure after cardiac hypertrophy or myocardial infarct, and nothing has been known especially about whether OSF-2 gene or OSF-2 protein acts as a factor promoting or inhibiting the progress of the pathology with the progress of the pathology of heart failure.

We thought that a novel therapeutic agent for heart failure could be developed by determining the relation of the expression of this gene in the heart to the pathology of heart failure, and accomplished the present invention after extensive studies.

Initially, we studied the expression of OSF-2 gene with the progress of the pathology of heart failure using aortostenotic rats, arteriovenous shunt rats and spontaneously hypertensive rats (SHR) to confirm that the variation in OSF-2 gene is not specific to Dahl heart failure model rats. As a result, all the models tested showed similar increased gene expression, strongly suggesting that such variations may be a universal event in the pathology of heart failure.

Then, OSF-2 gene was introduced into the rat heart in order to examine the action shown by OSF-2 gene on the heart. At first, a full-length rat OSF-2 gene was newly isolated, because rat OSF-2 gene had been so far unknown. The gene was inserted in a suitable expression vector, and introduced into rat heart. Echocardiography and hemodynamic tests showed that congestive cardiomyopathy-like pathology was induced in rats introduced with OSF-2 gene as demonstrated by thinned left ventricular wall, enlarged left ventricular lumen and decreased cardiac function, indicating that OSF-2 gene or OSF-2 protein is an aggravating factor of heart failure. The isolation of the rat gene is noteworthy because these analyses are difficult in other animals than rats. It was also shown that death by heart failure was retarded by introducing an antisense nucleotide inhibiting the expression of OSF-2 gene into the heart of a Dahl rat heart failure model. This revealed that heart failure is aggravated by the expression of OSF-2 gene or the production of OSF-2 protein concurrent with the progress of the pathology of heart failure, sufficiently suggesting that a drug containing a substance having the action of inhibiting the expression of OSF-2 gene or inhibiting the production or function of OSF-2 protein as an active ingredient inhibits aggravation of heart failure, which led to the present invention.

Accordingly, the present invention provides:

(1) a prophylactic or therapeutic agent for heart failure comprising a substance inhibiting the expression of OSF-2 gene or the production of OSF-2 protein or the function of OSF-2 protein or the function of a target molecule of OSF-2 protein as an active ingredient;

(2) a prophylactic or therapeutic agent for heart failure comprising a substance inhibiting the expression of OSF-2 gene as an active ingredient;

(3) a prophylactic or therapeutic agent for heart failure comprising a substance inhibiting the production of OSF-2 protein as an active ingredient;

(4) the prophylactic or therapeutic agent for heart failure as defined in (1) to (3) above wherein the substance inhibiting the expression of OSF-2 gene or the production of OSF-2 protein is an antisense nucleotide sequence;

(5) the prophylactic or therapeutic agent for heart failure as defined in (4) above wherein the antisense nucleotide sequence comprises nucleotides complementary to 12 or more contiguous nucleotides in the nucleotide sequence shown as SEQ ID NO: 5, 19, 20 or 21;

(6) the prophylactic or therapeutic agent for heart failure as defined in (5) above wherein the antisense nucleotide sequence comprises at least one sequence selected from the group consisting of SEQ ID NOs: 12-16;

(7) the prophylactic or therapeutic agent for heart failure as defined in (1) or (2) above wherein the substance inhibiting the expression of OSF-2 gene is a compound of the following general formula (I):

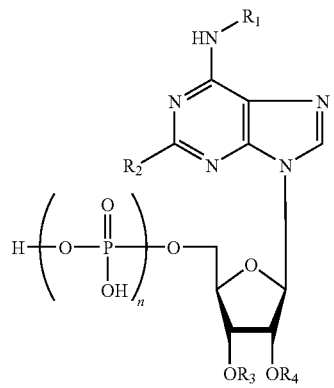

(I)

wherein $R_1$ represents a hydrogen atom, an optionally branched alkyl group or an aralkyl group in which the alkyl moiety may be branched, $R_2$ represents a hydrogen atom, a halogen atom or an amino group, $R_3$ and $R_4$ independently represent a hydrogen atom or an acyl group or $R_3$ and $R_4$ taken together represent an isopropylidene group, and n represents an integer of 0, 1, 2 or 3, or a biologically acceptable salt thereof;

(8) the prophylactic or therapeutic agent for heart failure as defined in (7) above wherein the substance inhibiting the expression of OSF-2 gene is a compound of general formula (I) above wherein both $R_3$ and $R_4$ represent a hydrogen atom;

(9) the prophylactic or therapeutic agent for heart failure as defined in (7) above wherein the substance inhibiting the expression of OSF-2 gene is a compound of general formula (I) above wherein $R_1$, $R_3$ and $R_4$ represent a hydrogen atom, $R_2$ represents a chlorine atom and n is 3;

(10) the prophylactic or therapeutic agent for heart failure as defined in (7) above wherein the substance inhibiting the expression of OSF-2 gene is a compound of general formula (I) above wherein $R_1$ represents a (2-methylphenyl)methyl group, $R_3$ and $R_4$ represent a hydrogen atom and n is 0;

(11) the prophylactic or therapeutic agent for heart failure as defined in (1) above comprising a substance inhibiting the function of OSF-2 protein as an active ingredient;

(12) the prophylactic or therapeutic agent for heart failure as defined in (1) above comprising a substance inhibiting the function of a target molecule of OSF-2 protein as an active ingredient;

(13) the prophylactic or therapeutic agent for heart failure as defined in (11) or (12) above wherein the substance inhibiting the function of OSF-2 protein or the function of a target molecule of OSF-2 protein is an antibody to OSF-2 protein or the target molecule of OSF-2 protein;

(14) a method for screening a substance having a prophylactic or therapeutic effect for heart failure comprising contacting a synthesized or genetically engineered substance or a natural substance or a derivative thereof with (1) a cell or an in vitro expression system having an expression regulatory region of OSF-2 gene and OSF-2 gene or a reporter gene or (2) OSF-2 protein or a target molecule of OSF-2 protein to detect the expression level of OSF-2 gene or the reporter gene or the amount of OSF-2 protein or the target molecule of OSF-2 protein;

(15) the method as defined in (14) above comprising contacting a synthesized or genetically engineered substance or a natural substance or a derivative thereof with a cell having an expression regulatory region of OSF-2 gene and OSF-2 gene to detect the expression level of OSF-2 gene;

(16) the method as defined in (14) above comprising constructing an expression vector having an expression regulatory region of OSF-2 gene linked upstream and/or downstream of the translation region of a reporter gene, then culturing a suitable host cell transfected with said vector, adding a synthesized or genetically engineered substance or a natural substance or a derivative thereof to the cultured cell and detecting the expression level of the reporter gene or the amount of the reporter protein after a given period;

(17) the method as defined in (14) above comprising contacting a synthesized or genetically engineered substance or a natural substance or a derivative thereof with OSF-2 protein or a target molecule of OSF-2 protein to detect the amount of the target molecule of OSF-2 protein or OSF-2 protein bound or unbound;
(18) the method as defined in (17) above comprising immobilizing OSF-2 protein or a target molecule of OSF-2 protein to a support and adding a synthesized or genetically engineered substance or a natural substance or a derivative thereof and the target molecule of OSF-2 protein or OSF-2 protein to the immobilized OSF-2 protein or target molecule of OSF-2 protein to detect the amount of the target molecule of OSF-2 protein or OSF-2 protein bound or unbound;
(19) a method for diagnosing heart failure comprising collecting a biological tissue and/or a body fluid and determining the expression level of OSF-2 gene in said tissue or determining a variation in OSF-2 gene or said regulatory region;
(20) a method for diagnosing heart failure comprising collecting a biological tissue and/or a body fluid and assaying OSF-2 protein or said fragment in said body fluid;
(21) a diagnostic reagent or a diagnostic kit for heart failure comprising a means for determining the expression level of OSF-2 gene or the production level of OSF-2 protein;
(22) a gene encoding a protein (a) or (b) below:
  (a) a protein comprising the amino acid sequence of SEQ ID NO: 6,
  (b) a protein comprising a variant of the amino acid sequence of SEQ ID NO: 6 in which one or several amino acids are deleted, substituted or added and having OSF-2 protein activity;
(23) a gene encoding a DNA (a) or (b) below:
  (a) a DNA comprising the nucleotide sequence of SEQ ID NO: 5,
  (b) a DNA hybridizing to the sequence of SEQ ID NO: 5 under stringent conditions and encoding a protein having OSF-2 protein activity;
(24) a recombinant protein (a) or (b) below:
  (a) a protein comprising the amino acid sequence of SEQ ID NO: 6,
  (b) a protein comprising a variant of the amino acid sequence of SEQ ID NO: 6 in which one or several amino acids are deleted, substituted or added and having OSF-2 protein activity;
(25) a non-human transgenic animal overexpressing OSF-2 gene and suitable for use as a pathologic model of heart failure;
(26) a method for evaluating or screening a substance capable of being an active ingredient of a prophylactic or therapeutic agent for heart failure using the non-human transgenic animal as defined in (25) above;
(27) a substance obtained by the method as defined in (14) to (18) or (26) above;
(28) a prophylactic or therapeutic agent for heart failure comprising the substance as defined in (27) above as an active ingredient;
(29) a method for treating heart failure comprising administering the substance as defined in (1) to (13) or (27) above;
(30) the method for treating heart failure as defined in (29) above comprising introducing an antisense nucleotide sequence of OSF-2 gene directly or incorporated into a vector (e.g. adenovirus-derived vector) or a liposome suitable for gene therapy;
(31) a use of the substance as defined in (1) to (13) or (27) above for the preparation of a prophylactic or therapeutic agent for heart failure.

DETAILED DESCRIPTION OF PREFERRED EMBODIMENTS

Figure 1:
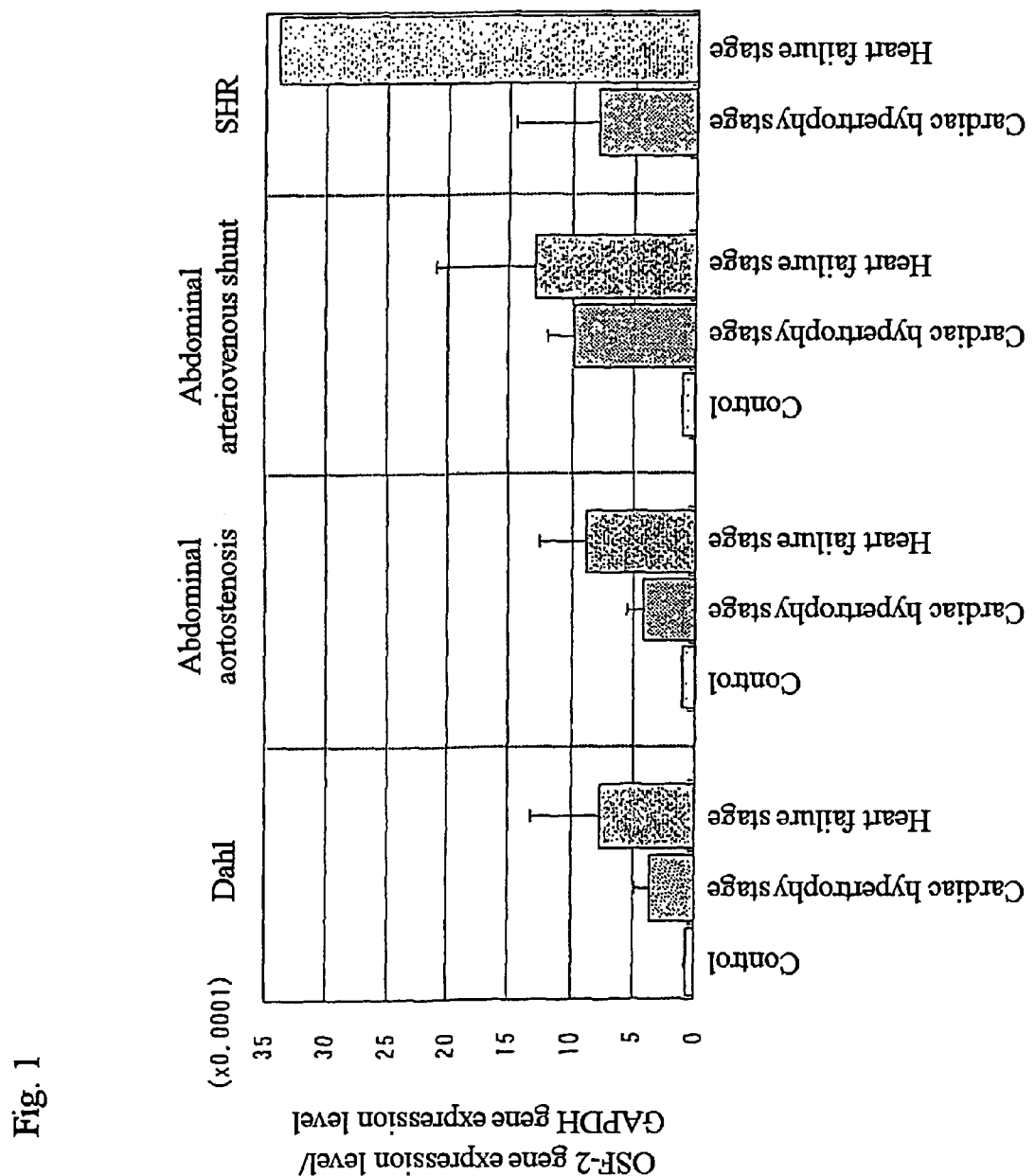
FIG. 1 shows expression levels of OSF-2 gene standardized by expression levels of GAPDH gene in various animal models.

The following substances (1) to (3) can be used as active ingredients of prophylactic or therapeutic agents for heart failure in the present invention.

(1) Substances Inhibiting the Expression of OSF-2 Gene

Substances inhibiting the expression of OSF-2 gene may be any of synthesized or genetically engineered compounds or natural compounds or derivatives thereof, including substances acting on a promoter or enhancer region of OSF-2 gene to inhibit the transcription of OSF-2 gene into mRNA (e.g., antisense nucleotides including DNA, RNA, phosphorothioate-type or other modified nucleotides and PNA (protein nucleic acid)), or substances having similar actions via a certain element in cells (such as a transcription factor) (e.g., substances binding to a transcription factor or a co-activator to inhibit binding to DNA or another transcription factors or co-activators).

The term "nucleotides" in reference to antisense nucleotides here means to include nucleotides produced from a naturally occurring bases and sugar moiety linked via proper phosphodiester bonds and analogs thereof. Thus, a first group included in this term encompasses naturally occurring species or synthetic species produced from naturally occurring subunits or homologs thereof. Subunits here refer to base-sugar combinations linked to adjacent subunits via phosphodiester bond or other bonds. A second group of nucleotides encompasses analogs of the first group, which mean residues having nucleotide-like functions but having a non-naturally occurring moiety. These include nucleotides chemically modified at the phosphate group, sugar moiety or 3' or 5' end to increase stability. Examples are phosphorothioate and methylphosphonate obtained by substituting a sulfur atom and —$CH_3$, respectively, for one of the oxygen atoms of the phosphodiester group between nucleotides. Nucleotide analogs containing purine and pyrimidine in the form of modified bases, i.e. other than normally found in nature can also be used.

Preferred antisense nucleotides for use in the present invention are nucleotides complementary to 12 or more contiguous nucleotides, preferably 16 or more contiguous nucleotides, more preferably 18 or more contiguous nucleotides in the nucleotide sequence shown as SEQ ID NO: 5, 19, 20 or 21. Especially preferred antisense nucleotides have at least one sequence selected from the group consisting of SEQ ID NOs: 12-16.

In the present invention, peptide nucleic acids (Bioconjug. Chem., 4 373-378, 1994) can also be used in place of antisense nucleotides.

Specific examples of compounds inhibiting the expression of OSF-2 gene include compounds of general formula (I) below or biologically acceptable salts thereof.

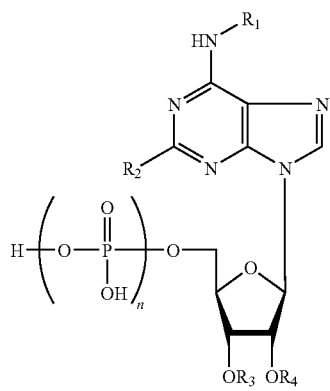

In the formula above, $R_1$ represents a hydrogen atom, an optionally branched alkyl group or an aralkyl group in which the alkyl moiety may be branched. Examples of the optionally branched alkyl group include methyl, ethyl, isopropyl, isobutyl and tert-butyl groups. In the case of the aralkyl group in which the alkyl moiety may be branched, the aryl moiety may be substituted by a lower alkyl group such as methyl, ethyl or propyl, a lower alkoxy group such as methoxy or ethoxy, a halogen atom, nitro, cyano, carboxyl, alkoxycarbonyl or the like. Representative examples include benzyl, (2-methylphenyl)methyl, (3-methylphenyl)methyl, (4methylphenyl)methyl, (2-chlorophenyl)methyl, (2-ethylphenyl)methyl, (2-methoxyphenyl)methyl, (2-methoxycarbonylphenyl)methyl, 2-phenethyl, (1-naphthyl)methyl, (2-naphthyl)methyl and 2-(2-naphthyl)ethyl groups. Among them, preferred examples for $R_1$ include a hydrogen atom and aralkyl groups in which the alkyl moiety may be branched, among which a hydrogen atom and a (2-methylphenyl)methyl group are especially preferred.

$R_2$ represents a hydrogen atom, a halogen atom or an amino group. Preferred examples for $R_2$ include a hydrogen atom and a chlorine atom.

$R_3$ and $R_4$ independently represent a hydrogen atom or an acyl group or $R_3$ and $R_4$ jointly represent an isopropylidene group. Examples of acyl groups include lower alkanoyl groups such as acetyl and propionyl.

n represents 0, 1, 2 or 3, among which 0 and 3 are especially preferred. When n is 1, 2 or 3, one or more hydrogen atoms in the phosphonate moiety may form a salt with an alkali metal or an alkali earth metal such as sodium, potassium, calcium or magnesium or an organic amine.

(2) Substances Inhibiting the Production of OSF-2 Protein

Substances inhibiting the production of OSF-2 protein may be any of synthesized or genetically engineered compounds or natural compounds or derivatives thereof, including substances inhibiting the translation of OSF-2 mRNA into OSF-2 protein by an antisense nucleotide sequence of OSF-2 gene. The term "nucleotide" in reference to antisense nucleotide here is as defined in (1) above. Antisense nucleotides include RNA, DNA, phosphorothioate-type or other modified nucleotides or PNA (protein nucleic acid) and can be designed to target any of the structural gene region, 3'-untranslated region, 5'-untranslated region or intron/exon junction of OSF-2 gene. Antisense strands can be introduced into a target tissue directly or by introducing a vector designed to be transcribed into antisense RNA.

Ribozymes recognizing a specific structure of OSF-2 mRNA to cleave it can also be used. Ribozymes are nucleic acid molecules having an enzymatic activity capable of cleaving other RNA molecules in a manner specific to a target nucleotide sequence and can be formed, for example, in hammerhead or hairpin motifs, (Nature, 324, 429, 1986; Ann. Rep. Med. Chem., 30 285-294, 1995; J. Med. Chem., 38, 2023-2037, 1995). Ribozymes may be introduced into a target tissue directly or in the form of a complex with a lipid or a liposome. Alternatively, a DNA or RNA vector expressing a ribozyme can be introduced into a target tissue.

(3) Substances Inhibiting the Function of OSF-2 Protein or Substances Inhibiting the Function of a Target Molecule of OSF-2 Protein In the present invention, substances inhibiting the function of OSF-2 protein or substances inhibiting the function of a target molecule of OSF-2 protein can be used in prophylactic or therapeutic agents for heart failure. The target molecule of OSF-2 protein means a molecule whose structure or activity is influenced by OSF-2 protein, including, but not limited to, substrates, binding partners and receptors.

Substances inhibiting the function of OSF-2 protein or substances inhibiting the function of a target molecule of OSF-2 protein may be any of synthesized or genetically engineered compounds or natural compounds or derivatives thereof, including substances inhibiting binding of OSF-2 protein to a target molecule (e.g. receptor) of OSF-2 protein on which OSF-2 protein acts, or substances inhibiting intracellular signal transduction to inhibit the activity of OSF-2 protein. Examples are antibodies against OSF-2 protein or antibodies against a target molecule of OSF-2 protein. The antibodies may be polyclonal or monoclonal. These antibodies can be prepared by, for example, purifying the protein from cultures of expression cells or recombinant host and immunizing a rabbit or the like with the purified protein together with a suitable adjuvant to obtain an antibody fraction from the serum according to standard methods. Alternatively, monoclonal antibodies can be prepared using mice or rats, or humanized antibodies or single-strand antibodies can be prepared using genetic engineering techniques or transgenic animals, although the present invention is not limited to these specific methods. The substances also include proteases specifically degrading OSF-2 protein or a target molecule of OSF-2 protein, inactivated OSF-2 protein (including variants) or decoys of OSF-2 target molecules and soluble receptor molecules.

When the substances (1) to (3) above are peptides, they also include peptide analogs having an enzyme-acting site modified to make drugs of the present invention unsusceptible or less susceptible to in vivo degradation by peptidases or proteases after administration to a subject. Said analogs include peptide analogs wherein one or more peptide bonds at the enzyme-acting site are replaced by another covalent bond or peptide analogs wherein one or more amino acids at the enzyme-acting site are D-amino acids.

Pharmaceutical Preparations

Pharmaceutical preparations containing the substances as described above as active ingredients are prepared using carriers or excipients or other additives used for standard formulation.

Active ingredients of pharmaceutical compositions of the present invention may be free acid or base, or pharmaceutically acceptable salts thereof Suitable salts include salts with inorganic acids such as hydrochloric acid, sulfuric acid and phosphoric acid or salts with organic acids such as formic acid, acetic acid, butyric acid, succinic acid and citric acid. Salts with metals such as sodium, potassium, lithium and calcium or salts with organic bases are also suitable.

Preferably, active ingredients are mixed with known pharmacologically acceptable carriers, excipients, diluents or the like and administered in a pharmaceutically conventional manner such as oral administration or parenteral administration including intravenous, intramuscular or subcutaneous administration. Pharmaceutical compositions of the present invention can be prepared by, for example, appropriately mixing an active ingredient with physiologically acceptable carriers, flavoring agents, excipients, stabilizers, diluents, emulsifiers, solubilizing agents, dispersing agents, syrups or the like and can be used as tablets, powders, granules, solutions, etc. Tablets can contain additives including, for example, binders such as gelatin and lubricants such as cornstarch, or can be coated with sugar or a gastric or enteric film. Capsules can be prepared by further including liquid carriers in said compositions. Sterile compositions for injection can also be prepared by applying conventional formulations. Aqueous solutions for injection include isotonic solutions containing glucose or the like and can be combined with suitable solubilizers such as polyethylene glycol. They may also contain buffers, stabilizers, preservatives, antioxidants, soothing agents and the like. When active ingredients are susceptible to degradation in the gastrointestinal tract via oral administration, they can be orally administered as formulations less susceptible to degradation in the gastrointestinal tract such as microcapsules enclosing active ingredients in liposomes, for example. They can also be adsorbed via non-gastrointestinal mucosa such as rectal, nasal or sublingual administration. In this case, they can be administered in the form of suppositories, nasal sprays or sublingual tablets.

For use in gene therapy, antisense nucleotides or the like can be integrated into known vectors suitable for gene therapy such as adenoviruses.

When pharmaceutical compositions of the present invention are therapeutically used, therapeutically effective doses are determined for each case depending on the age and the weight of the subject, the severity of the disease and the route of administration and other factors. Typically, the oral dose is about 0.1-1000 mg/adult/day, which may be administered once or divided into several subdoses. For continuous intravenous administration, the dose can range from 0.01 µg/kg/min to 1.0 µg/kg/min, preferably from 0.025 µg/kg/min to 0.1 µg/kg/min.

Screening Methods

Substances that can be used as active ingredients of prophylactic or therapeutic agents of the present invention can be screened as follows, for example.

OSF-2 gene or OSF-2 protein or derivatives thereof used for screening substances inhibiting the expression of OSF-2 gene or substances inhibiting the production of OSF-2 protein may be derived from any sources including mammals such as human, mouse, rat, rabbit, pig, dog, monkey and guinea pig. That is, they include known genes or proteins in addition to the newly found rat gene (SEQ ID NO: 5) or the protein encoded thereby (SEQ ID NO: 6). OSF-2 gene and OSF-2 protein of the present invention include various known splice variants of OSF-2 gene and proteins translated therefrom since various splice variants of OSF-2 gene are known. For example, murine OSF-2 genes and OSF-2 proteins include those shown as SEQ ID NO: 19 and human OSF-2 genes and OSF-2 proteins include those shown as SEQ ID NOs: 20 (from placenta) and 21 (from primary tumor). Partial sequences of OSF-2 gene can also be used alone or as a chimeric gene with another gene. Similarly, partial sequences of OSF-2 protein can be used alone or fused with another peptide.

Among them, human genes or proteins are preferably used for studies/developments of prophylactic or therapeutic agents for human. Those derived from animals such as mouse and rat are preferably used for studies/developments using animal models, i.e. non-human transgenic animals having heart failure condition due to forced expression of OSF-2 gene.

Substances inhibiting the expression of OSF-2 gene or substances inhibiting the production of OSF-2 protein are generally screened by methods using a reporter gene. Suitable reporter genes include, for example, chloramphenicol acetyl transferase (CAT), β-galactosidase (β-Gal) and luciferase. Substances inhibiting the expression of OSF-2 gene can be screened by, for example, constructing an expression vector having an expression regulatory region (promoter, enhancer or the like region) of OSF-2 gene linked upstream and/or downstream of the coding region of a reporter gene, transfecting said vector into a suitable culture cell, adding a test substance to the culture cell (said substance may be any of synthesized or genetically engineered compounds or natural compounds or derivatives thereof) and determining the expression level of the reporter gene or the amount of the reporter protein after a given period. The expression regulatory region of OSF-2 gene (promoter, enhancer or the like region) can be obtained from commercially available genomic libraries by plaque hybridization using a fragment of OSF-2 cDNA as a probe. In the examples below, for example, compounds inhibiting the expression of OSF-2 gene were found by introducing a "reporter vector" having a promoter region of OSF-2 gene linked upstream of a luciferase gene into COS-1 cells and assaying luciferase activity after adding a candidate compound. Substances of the present invention also include decoys, i.e. decoy-type nucleic acid drugs against transcription factors acting on OSF-2 gene (Science. 250, 997-1000, 1990) or the like. The amount of the reporter protein can be determined as enzymatic activity or the expression level of the protein using antibodies or the like.

Antisense nucleotides or ribozymes or the like inhibiting the production of OSF-2 protein can be screened by introducing the antisense nucleotides or ribozymes into culture cells expressing OSF-2 protein by e.g. electroporation or liposome techniques and determining the expression level of OSF-2 protein. In the examples below, for example, antisense nucleotides inhibiting the expression of OSF-2 protein were found by introducing a series of antisense nucleotides targeted on the initiation codon of OSF-2 into COS-1 cells overexpressing OSF-2 protein. Any antisense nucleotides having such an action may be suitable such as those inhibiting transcription, mRNA splicing or passage of mRNA through nuclear membrane. Similar methods can be used for screening ribozymes. Suitable culture cells include cells transfected with OSF-2 gene as well as any cells originally expressing OSF-2 gene such as MC3T3-E1 cells (Biochem.J. 294, 271-278, 1993) and the like.

Substances inhibiting the function of OSF-2 protein or substances inhibiting the function of a target molecule of OSF-2 protein can be screened by, for example, immobilizing either the target molecule of OSF-2 protein or OSF-2 protein to a plate or the like, and then adding a test substance (said substance may be any of synthesized compounds or natural compounds or derivatives thereof) and OSF-2 protein or a target molecule thereof, and determining the amount of OSF-2 protein or the target molecule of OSF-2 protein bound or unbound by ELISA, RIA, fluorescence labeling or the like. They can also be screened by using cells expressing a target molecule of OSF-2 with labeled OSF-2 and a test drug followed by a suitable washing treatment after a given period and then determining the number of labeled cells or the extent of labeling by FACS, absorbance, color development or other means. Alternatively, they can also be screened on the basis of the action shown by OSF-2 (e.g. adhesion activity) by adding a test substance (said substance may be any of synthesized compounds or natural compounds or derivatives thereof) into a culture medium of culture cells and determining the strength of the action shown by OSF-2.

Diagnostic Methods, Diagnostic Agents and Diagnostic Kits

OSF-2 gene was shown by the inventors of the present application to increase the expression level with aggravation of heart failure. The extent of aggravation of heart failure can be diagnosed by determining the expression level of OSF-2 gene using a biopsy sample of a patient with heart failure. For example, the expression level of OSF-2 gene can be determined by isolating total RNA from a biopsy sample of a patient using ISOGEN (Nippon Gene) and treating it with DNase, then synthesizing cDNA, amplifying OSF-2 gene by PCR using suitable primers and determining the intensity of the band corresponding to OSF-2 by gel electrophoresis. The expression of OSF-2 gene can also be determined by any other techniques for quantitatively measuring RNA or DNA such as the method described in Example 3, Northern hybridization or cDNA array techniques.

As OSF-2 gene was shown by the present invention to be an aggravating factor of heart failure, it can be readily predicted that individuals having some variation in OSF-2 gene or a regulatory region thereof tend to be susceptible to heart failure or aggravation in heart failure if the function of OSF-2 protein is enhanced or the gene expression level is increased by the presence of such variation. Thus, risk factors can be diagnosed by testing these variations in the gene. Variations in the gene can be detected by isolating DNA from a blood sample of a patient according to standard methods, determining the nucleotide sequence according to the method described in Examples 1-5 and comparing it with the normal sequence. Once the relation between a variation and heart failure has been clarified, the DNA chip or SSCP technique can be applied to specifically detect such a variation.

As OSF-2 is known to be a secretory protein, it is readily predicted that an increase in gene expression is accompanied by an increase in OSF-2 protein levels in the heart and blood. Thus, the extent of aggravation of heart failure can be known by assaying OSF-2 protein levels in the blood. Suitable assay methods include ELISA or RIA using antibodies against OSF-2, or HPLC or mass spectrometric assays. OSF-2 protein here may not be in a total form but may be fractionated so far as it can be assayed.

The present invention also include diagnostic agents or diagnostic kits for heart failure comprising a means for deterng the expression level of OSF-2 gene or the production level of OSF-2 protein using the assay means as described above.

Non-human Transgenic Animals Transfected with OSF-2 Gene

Non-human host animals for creating non-human transgenic animals having heart failure condition due to forced overexpression of OSF-2 gene in the present invention include small animals such as mouse, rat and rabbit as well as large animals such as dog, pig, sheep and cattle and any other animals expressing OSF-2 gene and showing the function or physiological action of OSF-2 protein. Suitable promoters for expressing OSF-2 gene include constitutively expressing promoters (CMV promoters, SV40 early promoters, etc.) as well as tissue-specific promoters (αXMHC promoters,α-actin promoters, etc.), inducibly expressing promoters (Cre-loxP system, tetracycline inducible system, ecdysone inducible system, etc.) and any other systems capable of inducing gene expression.

The present invention provides transgenic animals inducibly and heart tissue-specifically expressing OSF-2 gene. Suitable inducible expression systems include, for example, ecdysone inducible system (Proc Natl. Acad. Sci. U.S.A., 93 3346-3351, 1996; Nature, 366 476-479, 1993; Cell, 71, 63-72, 1992). This inducible expression system is designed to constitutively express ecdysone receptor and retinoid X receptor (RXR receptor) so that a receptor heterodimer consisting of both receptors binds to an ecdysone-responsive region in the presence of ecdysone to induce the expression of a target gene downstream thereof. For example, an "induction transgenic animal" expressing ecdysone receptor and RXR receptor and an "expression transgenic animal" expressing an ecdysone-responsive region and a target gene can be separately prepared and crossed to prepare a double transgenic animal. The target gene can be induced by administering ecdysone to this double transgenic animal.

Initially, a transgenic animal characterized by expressing OSF-2 protein is prepared by a standard method, which is an animal obtained by ontogenesis of totipotent cells transfected with a recombinant gene for preparing a transgenic animal obtained by linking OSF-2 gene downstream of an ecdysone responsive region (transgenic animal for expression) and progeny thereof.

On the other hand, a transgenic animal characterized by inducibly expressing an ecdysone receptor protein specifically in the heart tissue and an RXR protein systemically is prepared, which is an animal obtained by ontogenesis of totipotent cells transfected with a recombinant gene for preparing a transgenic animal having both an expression unit having an ecdysone receptor gene inked downstream of a heart tissue-specifically expressing promoter and an expression unit having RXR gene linked downstream of a non-tissue specific promoter and progeny thereof (transgenic animal for induction).

The totipotent cells here mean cells capable of potentially differentiating into any cells. In the case of mouse, for example, totipotent cells may be fertilized eggs and early embryos as well as culture cells such as pluripotent ES cells. DNA fragments can be introduced into culture cells by electrostatic pulsing, liposome, calcium phosphate and other techniques. Physical injection of DNA solutions into fertilized eggs (microinjection) is specially preferred.

Recombinant genes used in the processes for preparing a transgenic animal according to the present invention are desirably inserted during the embryogenic stage. Cells transfected with DNA are transplanted into an surrogate mother animal, which is fed and allowed to give birth to an intended offspring transgenic animal transfected with a desired gene (founder transgenic animal). The presence of the transgene can be confirmed by PCR or Southern blotting of somatic DNA isolated from a section of a part of the body of the animal (e.g. tail end).

Moreover, progeny animals of transgenic animals of the present invention can be prepared by further including the steps of crossing each founder transgenic animal and a normal animal to give F1 animals (progeny animals) and crossing transgenic animals expressing the trait among said F1 animals each other or with normal animals to give homozygous or heterozygous F2 animals (progeny animals). The inventors in fact have succeeded in preparing these transgenic animals.

Double transgenic animals can be obtained by crossing a transgenic animal for expression and a transgenic animal for induction and confirming the presence of both genes, and then transgenic animals inducibly and heart tissue-specifically expressing OSF-2 gene can be obtained by administering ecdysone to said double transgenic animals.

Transgenic animals of the present invention can be used for pathological studies and drug screening as models of diseases in which OSF-2 gene is involved (e.g. heart failure models).

Moreover, substances as active ingredients of prophylactic or therapeutic agents for diseases in which OSF-2 gene is involved (e.g. heart failure) can be evaluated or screened by administering a candidate substance to a transgenic animal of the present invention and determining the expression level of OSF-2 gene, the production of OSF-2 protein or changes in cardiac function, etc. Thus, the present invention also includes methods for evaluating or screening substances as active ingredients of prophylactic or therapeutic agents for diseases in which OSF-2 gene is involved using transgenic animals of the present invention.

Therapeutic agents for heart failure provided by the present invention exhibit their activity on the specific target and have efficacy based on a different mechanism from conventional ones for mild to severe heart failure in which OSF-2 gene or protein is involved. Screening methods of the present invention lead to the development of therapeutic agents for all diseases including heart failure in which OSF-2 gene or protein is involved. According to diagnostic methods of the present invention, the extent of aggravation or the risk of the onset of heart failure can be predicted, which helps improvements of lifestyle or treatments. Moreover, transgenic animals of the present invention can be used for pathological studies or drug screening as models of diseases in which OSF-2 gene is involved.

The following examples further illustrate the present invention. These examples are given for illustrative purposes, but are not construed as limiting the scope of the invention.

EXAMPLES

Example 1

Search for OSF-2 by Subtraction Method 1-1 Preparation of Pathologic Model Rats of Heart Failure and Collection of Left Ventricular Samples Male Dahl salt-sensitive rats (Dahl-S) (SHIMIZU LABORATORY SUPPLIES) were raised on an 8% high salt diet from 6 weeks of age, and the left ventricle was collected from three animals each at cardiac hypertrophy stage (11 weeks of age) and heart failure stage (14 weeks of age).

1-2 Preparation of mRNA

Total RNA was prepared from about 500 mg of said left ventricle using ISOGEN (Nippon Gene) as instructed by the manufacturer. Then, mRNA was purified from about 400 µg of the combined total RNA from three animals each at cardiac hypertrophy stage and heart failure stage using Fast Track 2.0 Kit (Invitrogen) as instructed by the manufacturer to recover about 3 µg of mRNA at each stage.

1-3 cDNA Subtraction cDNA subtraction was performed using PCR-Select cDNA subtraction kit (Clontech) as instructed by the manufacturer. That is, cDNA was synthesized from 2 µg of each mRNA obtained in 1-2 above and digested with restriction enzyme RsaI. Then, subtractive hybridization was performed using the cDNA synthesized from the left ventricle of animals at 14 weeks of age as tester cDNA and the cDNA synthesized from the animals at 11 weeks of age as driver cDNA after the 2 adapters included in the kit had been separately linked to the tester cDNA. Then, a cDNA fragment with altered expression level was specifically amplified by PCR using primers complementary to the adapters to give amplification product 1.

A similar subtraction operation was performed using the cDNA synthesized from the left ventricle of animals at 11 weeks of age as tester cDNA and the cDNA synthesized from the left ventricle of animals at 14 weeks of age as driver cDNA to give amplification product 2.

1-4 Dot Blot Screening

A. Preparation of Dot Blots

Amplification product 1 was TA cloned into PCR II vector (Invitrogen) to select clones having the insert fragment. One µl each of the PCR reaction solution in which the insert fragment of each clone had been amplified was heat-treated, and then dot-blotted on 2 nylon membrane filters (Boehringer) and fixed with UV crosslinker (Stratagene).

B. Preparation of cDNA Probes

Amplification product 1 was digested with restriction enzymes RsaI,EaeI and SmaI to remove the adapters and subjected to random prime labeling with DTG-dUTP using DIG High Prime DNA labeling/detection kit II (Boehringer) as instructed by the manufacturer to prepare cDNA probe 1. Similarly, cDNA probe 2 was prepared from amplification product 2.

C. Screening

One of the dot blot membranes prepared in A above was hybridized with cDNA probe 1 and the other with cDNA probe 2 (under the conditions of hybridization at 42° C. overnight in DIG Easy Hyb solution as instructed by Boehringer for DIG High Prime DNA labeling/detection kit II and washing twice with 2 x SSC, 0.1% SDS at room temperature for 5 minutes and twice with 0.1 x SSC, 0.1% SDS at 68° C. for 15 minutes) and reacted with alkaline phosphatase-labeled DIG antibodies in the blocking buffer included in the kit, and then CSPD ready-to use was added to develop chemiluminescence and X-ray film was exposed. Clones showing a stronger signal with cDNA probe 1 than cDNA probe 2 were selected as positive clones and sequenced.

1-5 Sequencing

The nucleotide sequences were determined by analysis on an automatic DNA sequencer model 373A (PE Applied Biosystems) using THERMO Sequenase™ II dye terminator cycle sequencing kit (Amersham Pharmacia). The resulted gene sequences were compared with GenBank databanks to reveal that one of the clones (SF014) was a gene having a 86% homology to mouse OSF-2 (GenBank Accession No. D13664).

Example 2

Cloning of Rat OSF-2 cDNA

Rat OSF-2 cDNA was isolated by screening 10 phage subpools of about 4000 clones (a total of about 40,000 clones) prepared from a rat aorta cDNA library (Clontech) inserted into λgt1 vector by PCR using primer (1) 5'-GTTCAT-TGAAGGTGGCGATGGTC-3' (SEQ ID NO: 1) and primer (2) 5'-GAGATAAAATCCCTGCATGGTCCT-3' (SEQ ID NO: 2) designed on the basis of the nucleotide sequence of SF014 to give 3 positive subpools. One of the subpools was screened by hybridization using the fragment amplified by the above mentioned PCR as a probe labeled with alkaline phosphatase using AlkPhos Direct™ (Amersham Pharmacia) to give one positive clone rat OSF-2#1. The insert fragment was integrated into the EcoRI site of pBluescript II (Stratagene) and the total nucleotide sequence was determined according to the method of Example 1-5.

The resulting clone had a length of about 3 kb corresponding to the nucleotide sequence from 292 to the 3' end of mouse OSF-2 (GenBank Accession No. D13664), suggesting that it was a 5'-truncated clone. Thus, SMART™ RACE cDNA Amplification Kit (Clontech) was used as instructed by the manufacturer to perform 5'-RACE reaction using rat aorta cDNA as a template and said primer (2) 5'-GAGATAAAATCCCTGCATGGTCCT-3' (SEQ ID NO: 2) and primer (3) 5'-CACGGTCGATGACATGGACAA-CACC-3' (SEQ ID NO: 3) designed on the basis of the nucleotide sequence of rat OSF-2#1. The resulting PCR product was TA cloned into PCR II vector of Invitrogen to give rat OSF-2 5RACE #1. The nucleotide sequence was determined according to the method of Example 1-5.

The results showed that rat OSF-2 5RACE #1 was a clone longer by about 300 bp than the initially obtained rat OSF-2#1 in the 5' direction with the 5' end being longer by 15 bp than the 5' end of mouse OSF-2 (GenBank Accession No. D13664). Ten phage subpools of about 40,000 clones (a total of about 400,000 clones) prepared from said rat aorta cDNA library were screened by PCR using primer (4) 5'-ACG-GAGCTCAGGGCTGAAGATG-3' (SEQ ID NO: 4) designed on the basis of the nucleotide sequence of rat OSF-2 5RACE #1 and said primer (3) 5'-CACGGTCGATGACATG-GACAACACC-3' (SEQ ID NO: 3) to give 2 positive subpools. One of the subpools was screened by hybridization using the fragment amplified by the above mentioned PCR as a probe to give one positive clone designated as rat OSF-2#2. The insert fragment was integrated into the EcoRI site of pBluescript II (Stratagene) and the nucleotide sequence was determined according to the method of Example 1-5.

The resulting clone had a length of about 2.6 kb with the 5' end being the same as that of the clone obtained with 5'-RACE and the 3' end corresponding to up to nucleotide 2410 of mouse OSF-2 (GenBank Accession No. D13664). The nucleotide sequence of rat OSF-2 5RACE #1 previously obtained was exactly the same as the nucleotide sequence of the relevant region of rat OSF-2#2. The full length of rat OSF-2 cDNA was completed by rat OSF-2#1 and rat OSF-2#2. The nucleotide sequence of this full-length cDNA and the ammo acid sequence translated from this nucleotide sequence are shown as SEQ ID NOs: 5 and 6.

Example 3

Analysis of the Expression of OSF-2 gene in various heart Failure model Rats

OSF-2 gene was selected by subtraction as a gene expressed at a higher level during heart failure stage in Dahl rats. This gene was tested for the extent to which it actually shows expression changes and whether or not it shows similar changes in various heart failure models other than Dahl rats.

3-1 Preparation of Model Rats and collection of samples

A. Dahl Heart Failure Model Rats

Male Dahl salt-sensitive rats (Dahl-S) (SHIMIZU LABORATORY SUPPLIES) were raised on an 8% high salt diet from 6 weeks of age, and the left ventricle was collected at cardiac hypertrophy stage (11 weeks of age) and heart failure stage (14 weeks of age). Dahl-S rats at 10 weeks of age raised on a normal diet were used as control.

B. Abdominal Aortostenotic Rats (Pressure Overload Model)

B-1. Procedure for Preparing a Pressure Overload Induced Cardiac Hypertrophy Rat Model Sprague-Dawley strain male rats at 9 weeks of age were used for experiments. After the rats were fixed in a prone position and abdominally incised under anesthesia by intraperitoneal administration of sodium pentobarbital (40 mg/kg), the abdominal aorta was exposed and dissected between the right and left renal arteries. A 21G needle was placed along the aorta and ligated with a silk suture together with the aorta between the right and left renal arteries, and then the needle was pulled out to form aortostenosis. In this model, the systolic blood pressure is raised by such abdominal aortostenosis, thus increasing the afterload of the heart to induce left ventricular hypertrophy.

B-2. Collection of samples

The systolic blood pressures at 3 and 17 months after the operation showed higher values than normal, i.e. 232 mmHg and 188 mmHg, respectively, due to arteriostenosis. At month 3, a significant increase in heart weight/body weight ratio was observed and the fractional shortening (FS) indicative of heart function decreased to 26% in rats at month 17 from 52% at month 3. Thus, the left ventricle was collected at 3 and 17 months after stenosis formation as samples of compensatory hypertrophy stage and uncompensated heart failure stage, respectively. Rats at 10 weeks of age were used as control.

C. Abdominal Arteriovenous Shunt Rats (Volume Overload Model)

C-1. Procedure for Preparing a Volume Overload Induced Cardiac Hypertrophy Rat Model Sprague-Dawley strain male rats at 9 weeks of age were used for experiments. After the rats were fixed in a prone position and abdominally incised under anesthesia by intraperitoneal administration of sodium pentobarbital (40 mg/kg), the abdominal aorta and cava were exposed and the bloodstream was stopped by clamping at the aortic bifurcations to the renal artery and the femoral artery. An 18 G needle was inserted into the aorta at the clamped sites to penetrate into the cava, thereby forming an arteriovenous shunt. The needle was pulled out and the wound in the aorta was closed with a surgical adhesive and the clamps were removed. After confirming that arterial blood flows into the vein in the shunt, the abdomen was closed. In this model, the formation of such an abdominal arteriovenous shunt induces an increase in venous pressure, and therefore an increase in cardiac preload to impose overload successively on the right atrium, right ventricle, left atrium and left ventricle, leading to hypertrophy. Moreover, low compliance in the venous system causes blood retention to induce pulmonary congestion.

C-2. Collection of Samples

Heart function was determined by echocardiography at 3 and 11 months after the operation, and then the animals were dissected to test the heart weight and autopsy findings. Rats at 11 months as compared with 3 months after the operation showed decreased hematocrit values and pulmonary edema in every case, suggesting advanced volume overload. The right heart system showed an increase in heart weight/body weight ratio or lung weight/body weight ratio, suggesting edema in the region from the right ventricle to the lung. The FS decreased from 57% to 31%. Therefore, the left ventricle was collected at 3 and 11 months after shunting as samples of compensatory stage and uncompensated heart failure stage, respectively. Rats at 10 weeks of age were used as control.

D. Spontaneously Hypertensive Rats (Pressure Overload Model)

SHR rats known as spontaneously hypertensive rats were raised and measured for blood pressure and echocardiogram over time. SHR at 3 months of age showed higher blood pressure and heart weight/body weight ratio than normal and suffered from cardiac hypertrophy due to hypertension. Animals at 19 months of age had appearances such as piloerection and squatting as well as lowered FS from 56% to 32% and lowered systolic blood pressure, and suffered from heart failure. Symptoms such as pleural fluid and edema were also found. The left ventricle was collected by dissection at each stage.

3-2 Analysis of Gene Expression

Gene expression was analyzed by a real-time PCR assay system using ABI PRISM 7700 (PE Applied Biosystems).

Total RNA was prepared from left ventricle of each model using ISOGEN (Nippon Gene) as instructed by the manufacturer and treated with DNase. TaqMan® Reverse Transcription Reagents (PE Applied Biosystems) were used to synthesize cDNA from 1 µg each of the total RNA treated with DNase in 50 µl of the reaction solution. The primers for detecting OSF-2 and the TaqMan probe used were (5) 5'-TG-CAAAAAGAGGTCTCCAAGGT-3' (SEQ ID NO: 7), (6) 5'-AGGTGTGTCTCCCTGAAGCAGT-3' (SEQ ID NO: 8), and (7) 5'-FAM ACAAAGTTCATTGAAGGTGGCGATG-GTC TAMRA-3' (SEQ ID NO: 9) designed on the basis of the nucleotide sequence of rat OSF-2 cDNA using a primer design software, ABI PRISM Primer Express. GAPDH used as an internal standard was detected with TaqMan® Rodent GAPDH Control Reagent (PE Applied Biosystems). The calibration curve for OSF-2 was prepared by serial dilution using SF014 described in Example 1 as a control plasmid, and the caliblation curve for GAPDH was prepared by serial dilution using a PCR product obtained by amplifying a partial sequence of rat GAPDH as a control plasmid after TA cloning into PCR II vector (1Invitrogen) to confirm the nucleotide sequence.

Real-time PCR assay reaction was performed with 0.4-0.8 µl of said cDNA as a template in 40 µl of the reaction solution using TaqMan® Universal PCR Master Mix (PE Applied Biosystems) as instructed by the manufacturer. The analytic results were standardized as the amount of GAPDH used as an internal standard and shown in FIG. 1. The results showed that the expression of OSF-2 increased with the progress of the pathology of heart failure in all the models.

Example 4

Construction of an Myc-His-rOSF-2 fused protein expression vector

An expression vector having an Myc epitope and 6 histidine tags at the carboxyl terminus of the protein translated from the coding region of rat OSF-2 gene and having a CMV promoter was prepared.

Initially, a fragment of about 500 bp obtained by digesting rat OSF-2 5RACE #1 obtained in Example 2 with restriction enzymes EcoRI and HindIII and a fragment of about 2780 bp obtained by digesting rat OSF-2#1 obtained in Example 2 with restriction enzymes HindIII and HpaI were ligated to a vector fragment obtained by digesting pTracer-CMV2 vector (Invitrogen) with restriction enzymes EcoRI and EcoRV using a ligation kit (TAKARA SHUZO) to give a plasmid designated as pTracer-CMV2/rOSF-2. Thus prepared pTracer-CMV2/rOSF-2 was digested with restriction enzymes EcoRI and SmaI to give a fragment of about 2330 bp containing the coding region of rat OSF-2 gene. Separately, PCR was performed using rat OSF-2#1 obtained in Example 2 as a template and primer (8) 5'-GACCCGGGAAGAACG-CATCATC-3' (SEQ ID NO: 10) designed on the basis of the sequence of the template and primer (9) 5'-TGGGTGAC-CCTGAGAACGGCCTTCTCTTGATC-3' (SEQ ID NO: 11) designed to insert a BstEII site immediately before the stop codon of rat OSF 2 and the amplification product was purified and then digested with restriction enzymes SmaI and BstEII to give a fragment of about 270 bp. These two fragments were ligated to a vector fragment obtained by digesting a plasmid for constructing an expression vector pcDNA4/Myc-His/type C (Invitrogen) with restriction enzymes EcoRI and BstEII using a ligation kit (TAKARA SHUZO) to give a plasmid designated as pcDNA4/Myc-His/rOSF-2. The total nucleotide sequence of the insert was confirmed by the method described in Example 1-5.

Example 5

Construction of an rOSF-2 Protein Expression Vector

An expression vector containing the total coding region of rat OSF-2 gene obtained in Example 2 and a CMV promoter was prepared. The pTracer-CMV2/rOSF-2 obtained in Example 4 was digested with restriction enzymes EcoRI and PmeI to give a fragment of about 3300 bp containing the coding region of rat OSF-2 gene, and this fragment was ligated to a vector fragment obtained by digesting said pcDNA4/Myc-His/type C (Invitrogen) with restriction enzymes EcoRI and PmeI using a ligation kit (TAKARA SHUZO) to give a fragment designated as pcDNA4/rOSF-2. The total nucleotide sequence of the insert was confirmed by the method described in Example 1-5.

Example 6

Functional Analysis by Transfection of OSF-2 Gene Into The Rat Heart 6-1 Large Scale Purification of Expression Plasmids The *E. coli* strain DH5α was transformed the expression plasmid(pcDNA4/rOSF-2) which prepared in Example 5 and amplified, and purified with EndoFree™ Plasmid Giga kit (QIAGEN), and then dissolved in phosphate-bufferd saline.

6-2 Preparation of HVJ-liposomes

50 µl of HMG-1, -2 mixture (1 mg/ml, Wako Pure Chemical Industries) was added, to 200 µg of said plasmid solution, and the mixed solution was left at room temperature for 1 hour and then supplied with a BSS solution to a total volume of 200 µml. The mixed solution was added to a glass tube containing a mixed lipid stored at −20° C. (Avanti Polar Lipid Inc., Sigma, Hum. Gene Ther. 8 (17), 2133-2141 (1997), Cell biology, a laboratory hand book, 2nd edition, vol. 4, 122-123 (1998)) and the tube was vigorously shaken on a vortex mixer for 30 seconds and allowed to stand in an incubator at 37° C. for 30 seconds. After 8 cycles of this operation, the glass tube was ultrasonicated for 6 seconds in an ultrasonic generator filled with water and shaken again for 30 seconds on a vortex mixer (120 rpm). Then, 1 ml of HVJ (20000 HAU or higher) (Kaneda: HVJ-liposome method Experimental Procedures for Gene Transfer & Expression Analysis; Yodosha) 70-79 (1997), Saeki, Kaneda: HVJ-liposome vector (Gene Therapy, Handbook for Development and Study: eds. Japan Gene Therapy Association) 429-438 (1999), Hum. Gene Ther. 8 (17), 2133-2141 (1997), Cell biology, a laboratory hand book, 2nd edition, vol. 4, 122-123 (1998)) was dispensed in a plastic dish of 30 mm of diameter and inactivated by irradiation with UV rays at 1980 mJ/cm$^2$ while the cover of the dish being open in a UV crosslinker. This inactivated HVJ was added to the glass tube and placed on ice for 10 minutes, and added 1.3 ml of BSS, and then shaken in a shaking incubator at 37° C. for 1 hour. Then, the total volume of the HVJ-liposome solution (from the glass tube) was gently overlaid on 7.5 ml of a 30% sucrose solution in a 10 ml ultracentrifugal tube and ultracentrifuged at 62,800×g, 4° C. for 1.5 hours. HVJ-liposomes accumulated as white particles on the sucrose solution were recovered with a Pasteur pipette and diluted with BSS to a total volume of 3 ml and then stored at 4° C.

6-3 Gene Transfection Into rats

The HVJ-hposome/DNA solution (at a concentration of 6.7 μg/ml) was injected into the left ventricle of the heart (apical and lateral sites) of 12-weeks old Sprague-Dawley rats (male) in an amount of 100 μl each at 3 sites (a total volume of 300 μl) using a 30-gauge needle (rOSF-2 group). As a control, pcDNA4/His-Myc vector was injected in the same manner (control group).

6-4 Echocardiography

After anesthesia with ketamine (50 mg/ml) and xylazine (10 mg/ml) at 6 weeks post transfection, echocardiography was performed using Core Vision Pro SSA 350A (probe: 7 MHz, Toshiba). The results are shown in Table 1, revealing that cardiac dilatation was induced in rOSF-2 group as demonstrated by significant differences in LVIDD (inner diameter of the end-diastolic left ventricle) and LVIDS (inner diameter of the end-systolic left ventricle) as compared with control group.

TABLE 1

Results of echocardiography (after 6 weeks)

| Evaluation items | Control | rat OSF-2 |
|---|---|---|
| n | 11 | 10 |
| IVSTD (mm) | 2.06 ± 0.08 | 1.69 ± 0.06# |
| LVIDD (mm) | 5.78 ± 0.16 | 7.68 ± 0.20# |
| LVPWD (mm) | 2.34 ± 0.09 | 1.98 ± 0.05# |
| IVSTS (mm) | 2.56 ± 0.13 | 2.44 ± 0.08 |
| LVIDS (mm) | 2.54 ± 0.18 | 3.81 ± 0.28# |
| LVPWS (mm) | 2.90 ± 0.12 | 2.87 ± 0.07 |
| EDV (μl) | 166.8 ± 10.6 | 316.9 ± 17.1# |
| ESV (μl) | 25.1 ± 4.4 | 67.1 ± 11.5# |
| FS (%) | 56.3 ± 2.5 | 50.8 ± 2.7 |

P < 0.01 vs. control
Abbreviations:
IVSTD: thickness of the end-diastolic interventricular septum
LVIDD: inner diameter of the end-diastolic left ventricle
LVPWD: thickness of the posterior wall of the end-diastolic left ventricle
IVSTS: thickness of the end-systolic interventricular septum
LVIDS: inner diameter of the end-systolic left ventricle
LVPWS: thickness of the posterior wall of the end-systolic left ventricle
EDV: end-diastolic volume
ESV: end systolic volume
FS: fractional shortening of the inner diameter of the left ventricle.

6-5 Hemodynamic Tests

After anesthesia with pentobarbital hydrochloride (50 mg/ml) at 6 weeks post transfection, intracardiac pressure and blood pressure were measured. The results are shown in Table 2. As compared with control group, significant differences were obtained in LVP (left ventricular pressure), LVEDP (left ventricular end-diastolic pressure), +LVdP/dT and —LVdP/dT in rOSF-2 group, suggesting decreased cardiac function.

TABLE 2

Hemodynamic tests (after 6 weeks)

| Evaluation items | Control | rat OSF-2 |
|---|---|---|
| n | 10 | 10 |
| BW (g) | 411.8 ± 6.9 | 415.6 ± 12.3 |
| HW (g/kg) | 2.63 ± 0.08 | 2.67 ± 0.12 |
| LVW (g/kg) | 1.97 ± 0.04 | 1.99 ± 0.04 |
| HR (beats per minute) | 444 ± 8 | 417 ± 12 |
| MBP (mmH) | 128.7 ± 4.7 | 119.7 ± 5.4 |
| LVP (mmHg) | 171.1 ± 7.1 | 143.5 ± 8.7# |
| LVEDP (mmHg) | 0.16 ± 0.07 | 1.00 ± 0.30# |
| +LVdP/dt (mmHg/sec) | 8511 ± 468 | 6120 ± 466# |
| −LVdP/dt (mmHg/sec) | 7356 ± 226 | 5580 ± 470# |

P < 0.01 vs. control
Abbreviations:
BW: body weight,
HW: heart weight,
LVW: left ventricle weight,
HR: heart rate,
MBP: mean blood pressure,
LVEDP: left ventricular end-diastolic pressure
LVP: left ventricular pressure
LVdP/dT: primary differentiation of maximum left ventricular pressure.

Example 7

Design and Selection of Antisense Oligonucleotides of OSF-2 Gene 7-1 Design of Antisense Nucleotide sequences Five antisense nucleotide sequences shown as SEQ ID NOs: 12-16 were designed by selecting regions containing an initiation codon AUG but not containing three continuous guanines (triplet G) and incapable of forming a hairpin structure or self-annealing and synthesized by an outer contractor. All the antisense nucleotide sequences are phosphorothioate type.

7-2 Selection of Antisense Nucleotide Sequences

The Myc-His-rOSF-2 fused protein expression vector pcDNA4/Myc-His/rOSF-2 described in Example 5 was introduced into COS-1 cells, and the antisense nucleotide sequences prepared in 1 above were introduced to screen antisense nucleotide sequences inhibiting the expression of Myc-His-rOSF 2 fused protein. The expression level of Myc-His-rOSF-2 fused protein was assayed by ELISA (Enzyme-Linked Immunosorbent Assay) using a Myc-specific monoclonal antibody (Invitrogen). Specifically, COS-1 cells were plated on a 96-well plate at a density of 2×10$^4$ cells/well. After 16-24 hours, 320 ng of DNA (pcDNA4/Myc-His/rOSF-2) was dissolved in OPTI MEM I medium (GIBCO) and mixed with the same amount of OPTI-MEM I medium containing 1 μl of LipofectAMINE 2000 reagent (GIBCO), and the mixture was reacted at room temperature for 20 minutes, and then added to COS-1 cells and incubated at 37° C. for transfection. Then, a series of antisense nucleotide sequences dissolved in phosphate-bufferd saline were added to a final concentration of 100 nM 1-4 hours after the addition of DNA and the mixture was incubated for further 3 days at 37° C.

The culture supernatant was immobilized to an EIA/RIA plate (Costar) by incubating 50 μl thereof at 37° C. for 1-2 hours, and washed twice with 200 μl of Dulbecco's phosphate-buffered saline containing 0.1% Tween (PBST). In order to block non-specific adsorption, the plate was treated with a blocking solution (PBST containing 1% bovine serum albumin) at 37° C. for 1 hour and washed with 200 μl of PBST three times. Then, a horseradish peroxidase-labelled anti-Myc monoclonal antibody (Invitrogen) diluted to 1:4000 in 50 μl of the blocking solution was coupled to the plate by incubation at room temperature for 1 hour and washed with 200 μl of PBST three times and with PBS once. After incubation with 50 μl of TMB (3,3',5,5'-tetramethylbenzidine) reagent (KPL) at room temperature for 30 minutes, the reaction was stopped by adding 50 μl of 0.1 N sulfuric acid and the absorbance at 450 nm was measured with a microplate reader.

Figure 2:
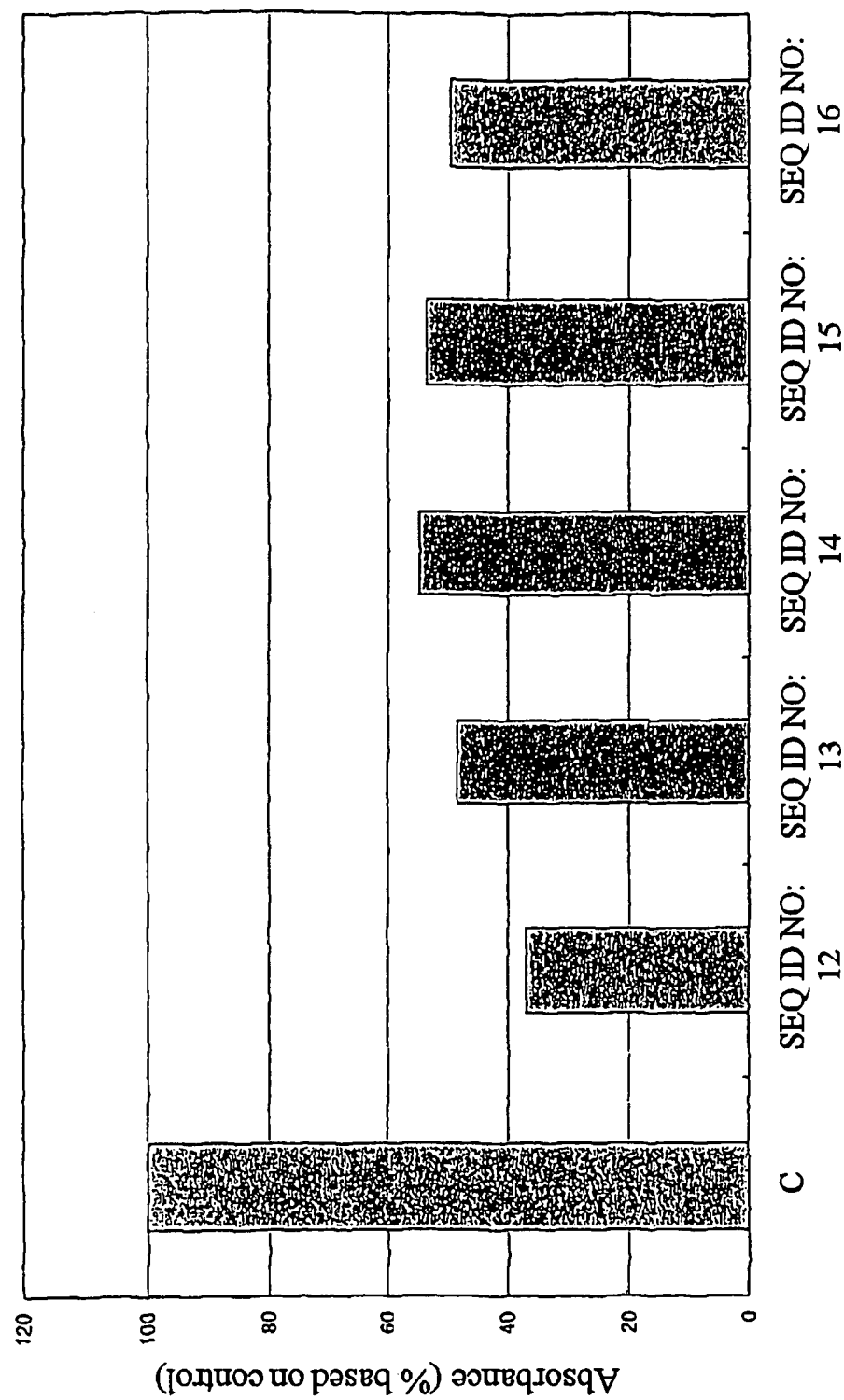
FIG. 2 shows inhibitory activities against OSF-2 protein production of the antisense nucleotide sequences of SEQ ID NO: 12 to 16. C means a control.

As a result, a series of antisense nucleotide sequences targeted on the initiation codon all had inhibitory activity against OSF-2 protein production, among which the antisense nucleotide sequence shown as SEQ ID NO: 12 inhibited the expression the most strongly, as shown in FIG. 2.

Figure 3:
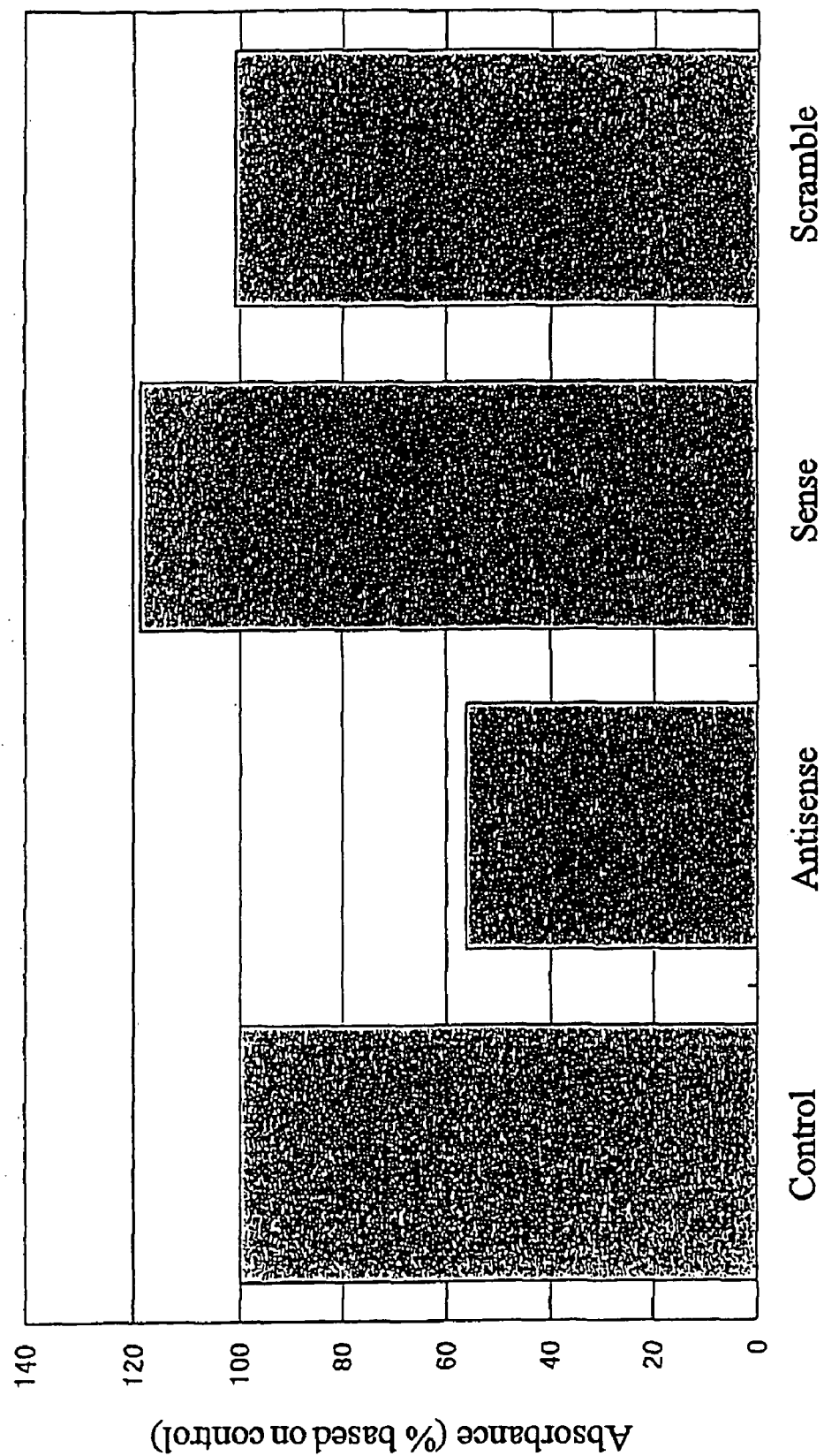
FIG. 3 shows inhibitory activities against OSF-2 protein production of an antisense nucleotide sequence (SEQ ID NO: 12), a sense nucleotide sequence (SEQ ID NO: 17) and a scramble nucleotide sequence (SEQ ID NO: 18).

Then, a sense nucleotide sequence that is a sense strand corresponding to SEQ ID NO: 12 (SEQ ID NO: 17) and a scramble nucleotide sequence with the 5', 3' direction reversed to SEQ ID NO: 12 (SEQ ID NO: 18) were prepared and subjected to experiments as described above at a final concentration of each nucleotide of 10 nM. The results showed that antisense nucleotide sequences had stronger inhibitory activity against OSF-2 protein production than the sense and scramble nucleotide sequences, as shown in FIG. 3.

solution selected in Example 7. Sense and scramble nucleotide sequences were also prepared in the same manner.

8-2 Gene Transfection into Rats

The HVJ-liposome/DNA solution was injected into the left ventricle of the heart (apical and lateral sites) of 13-weeks old Sprague-Dawley rats (male) in an amount of 100 μl each at 3 sites (a total volume of 300 μl) using a 30-gauge needle (rOSF-2/antisense group, rOSF-2/sense group and rOSF-2/scramble group). Similarly, pcDNA4/rOSF-2 was injected as a positive control group and pcDNA4/His-Myc vector was injected as a negative control group.

8-3 Echocardiography

After anesthesia with ketamine (50 mg/ml) and xylazine (10 mg/ml) at 3 weeks post transfection, echocardiography was performed using Core Vision Pro SSA 350A (probe: 7 MHz, Toshiba). The results are shown in FIG. 3, revealing that rOSF-2/antisense group inhibited cardiac dilatation similarly to negative control group (control) as demonstrated by significantly smaller LVIDD (inner diameter of the end-diastolic left ventricle) and LVIDS (inner diameter of the end-systolic left ventricle) as compared with positive control group (rOSF-2) or rOSF-2/sense group and rOSF-2/scramble group.

TABLE 3

Results of echocardiography

| Evaluation item | Control | rat OSF-2 | antisense | sense | scramble |
| --- | --- | --- | --- | --- | --- |
| n | 6 | 6 | 6 | 7 | 5 |
| IVSTD (mm) | 1.80 ± 0.11 | 1.30 ± 0.17* | 1.68 ± 0.12 | 1.26 ± 0.07* | 1.26 ± 0.12* |
| LVIDD (mm) | 6.18 ± 0.23 | 7.90 ± 0.29* | 6.42 ± 0.09# | 7.93 ± 0.18* | 7.60 ± 11* |
| LVPWD (mm) | 2.22 ± 0.11 | 1.45 ± 0.15* | 2.20 ± 0.13# | 1.46 ± 0.11* | 1.68 ± 0.07* |
| IVSTS (mm) | 3.15 ± 0.13 | 2.60 ± 0.17* | 3.07 ± 0.16 | 2.50 ± 0.07* | 2.60 ± 0.15* |
| LVIDS (mm) | 3.07 ± 0.16 | 3.95 ± 0.24* | 3.25 ± 0.15# | 4.24 ± 0.22* | 4.06 ± 0.18* |
| LVPWS (mm) | 2.92 ± 0.10 | 2.42 ± 0.16* | 2.80 ± 0.17 | 2.30 ± 0.15 | 2.66 ± 0.07* |
| EDV (μl) | 194.7 ± 16.8 | 338.0 ± 26.8* | 210.0 ± 6.8# | 339.2 ± 17.9* | 307.6 ± 10.4* |
| ESV (μl) | 37.8 ± 4.9 | 69.8 ± 9.8* | 43.3 ± 5.1# | 82.4 ± 10.2* | 73.4 ± 7.5* |
| FS (%) | 50.5 ± 1.1 | 50.1 ± 1.8 | 49.5 ± 1.7 | 46.7 ± 1.6 | 46.7 ± 1.6 |

*$P < 0.05$ vs. control
$P < 0.05$ vs. rat OSF-2
Abbreviations:
IVSTD: thickness of the end-diastolic interventricular septum
LVIDD: inner diameter of the end-diastolic left ventricle
LVPWD: thickness of the posterior wall of the end-diastolic left ventricle
IVSTS: thickness of the end-systolic interventricular septum
LVIDS: inner diameter of the end-systolic left ventricle
LVPWS: thickness of the posterior wall of the end-systolic left ventricle
EDV: end-diastolic volume
ESV: end-systolic volume
FS: fractional shortening of the inner diameter of the left ventricle.

Example 8

Inhibition of the Expression of OSF-2 Gene by Antisense Nucleotides 8-1 Preparation of HVJ-liposomes HVJ-liposomes were prepared as described in Example 6 by adding 50 μl of HMG-1,-2 mixture (1 mg/ml, Wako Pure Chemical Industries) to 200 μg of the plasmid solution prepared in Example 6.1 and 1.4 mg of the antisense nucleotide

Example 9

Inhibition of the Onset of Heart Failure by Antisense Nucleotides 9-1 Preparation of HVJ-liposomes HVJ-liposomes were prepared as described in Example 6.2 by adding 50 μl of HMG-1,-2 mixture (1 mg/ml, Wako Pure Chemical Industries) to 1.4 mg of a solution of the antisense nucleotides selected in Example 7 dissolved in BSS buffer. Sense nucleotides were also prepared in the same manner.

9-2 Gene Transfection into Rats

The HVJ-liposome/DNA solution was injected into the left ventricle of the heart (apical and lateral sites) of 13-weeks old Dahl-S rats (DIS/Eis, Eisai, male) raised on an 8% salt diet from the age of 8 weeks in an amount of 75 μl each at 4 sites (a total volume of 300 μl) using a 30-gauge needle (antisense group: 13 rats, sense group: 13 rats). After transfection, the rats were continuously raised on an 8% salt diet and the survival rate was tested to show an improvement in survival rate 30 weeks post transfection in antisense group (100%) as compared with sense group (61.5%).

Example 10

Preparation of Human OSF-2 Reporter Plasmids 10-1 Cloning of an Upstream Region of Human OSF-2 Gene Ten subpools of about 25,000 clones (a total of about 250,000 clones) prepared from a human genomic library (Clontech) inserted into EMBL-3 vector were screened by PCR using primer (10) 5'-AAGAATATTAAAAGT-TATTTGTGGGCAGGAGACAGATG-3' (SEQ ID NO: 22) and primer (11) 5'-CATTTAAAAGCCTATCAAGTGT-CAGGTCCACTCTC-3' (SEQ ID NO: 23) designed on the basis of the nucleotide sequence of a draft sequence containing an upstream region of human OSF-2 gene (GenBank Accession No. AL138679) to identify two positive subpools, and these subpools were screened by hybridization using the fragment amplified by the above mentioned PCR as a probe labeled with alkaline phosphatase using AlkPhos Direct™ (Amersham Pharmacia) to give two positive clones human OSF-2 genes #1, 2. The insert fragment in human OSF-2 gene #2 was integrated into the XhoI recognition site of pBluescript II (Stratagene) to give pB-hOSFg#2, which was partially sequenced according to the method of Example 1-5. The resulting clone had a length of about 13.5 kb corresponding to nucleotides 16397-30002 of the human draft sequence (GenBank Accession No. AL138679 version 11) and contained a region upstream of intron 2 of human OSF-2 gene. The total nucleotide sequence was determined from the SpeI recognition site located about 2 kb upstream of the initiation codon (ATG) to the initiation codon. This nucleotide sequence of about 2 kb is shown as SEQ ID NO: 24. This nucleotide sequence of about 2 kb contained variations in 4 bases as compared with the sequence of GenBank Accession No. AL138679 version 11 at nucleotides 764 G (T), 936 T (C), 1099 C m and 2106 G (C) starting from the SpeI recognition site (with the nucleotide in AL138679 version 11 shown in parentheses).

10-2 Preparation of Human OSF-2 Reporter Plasmids

A region extending from about 2 kb upstream of the initiation codon to immediately before the initiation codon was amplified by PCR using human OSF-2 gene #2 obtained in Example 10-1 as a template and primers (12) 5'-TGAG-CATATATCATGCTTTC-3' (SEQ ID NO: 25) and (13) 5'-AATCATCTCGAGTCTCTCCGTTGCAGT-TAGTCCCC-3' (SEQ ID NO: 26). Primer (13) was designed to insert a restriction enzyme XhoI recognition site into the 5' end, and this amplified fragment was digested with restriction enzymes SpeI and XhoI to give a fragment of about 2 kb, which was then ligated to a vector fragment of pGL3-enhancer (Promega) digested with restriction enzymes NheI and XhoI located upstream of the luciferase gene using a ligation kit (TAKARA SHUZO CO., LTD.) to give pGL3-hOSFgE. The nucleotide sequence of the insert was determined according to the method of Example 1-5 to confirm that it was identical with the nucleotide sequence determined in Example 10-1.

Example 11

Screening of Compounds Influencing the Expression of Human rOSF-2 Gene 11-1 Reporter Assay Using COS-1 Cells COS-1 cells were plated on a 96-well plate at a density of $3 \times 10^4$ cells/well and the plate was incubated at 37° C. for 16-24 hours and then transiently transfected with OSF-2 reporter plasmid pGL3-hOSFgE shown in Example 10 using LipofectAMINE 2000 reagent (GIBCO), and after incubation for 24 hours at 37° C., the medium was replaced. After 24 hours, candidate compounds were added and after further 24 hours, luciferase activity was assayed. Luciferase activity was assayed according to the protocol of a luciferase assay system (Promega) and detected with 1420 multilabel counter (Wallac). Similar experiments were performed on pGL3-control (Promega) containing a luciferase gene linked to the downstream of SV40 promoter as a control. A number of compounds were screened by this method to show that 2-chloroadenosine 5'-triphosphate tetrasodium and Metrifudil (N-[(2-methylphenyl)methyl]-adenosine) inhibit luciferase activity specifically to OSF-2 promoter. These compounds have the following chemical structural formulae.

2-Chloroadenosine 5'-triphosphate tetrasodium:

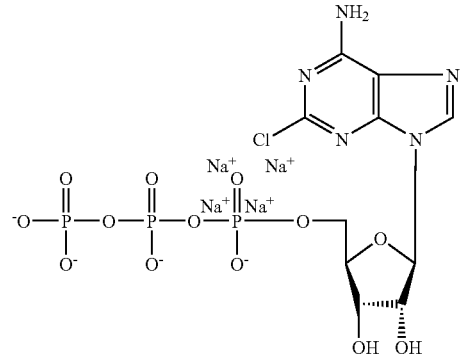

Metrifudil (N-[(2-methylphenyl)methyl]-adenosine):

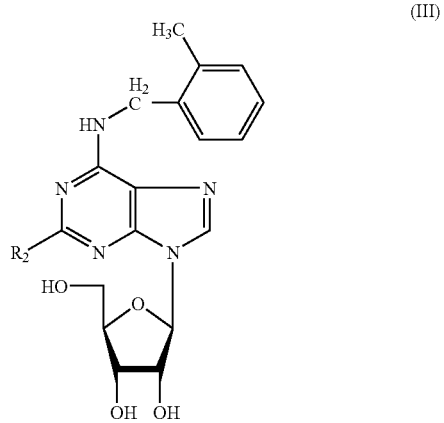

11-2 Expression Analysis Using MC3T3-E1 Cells

Murine osteoblast-like cells MC3T3-E1 (purchased from RIKEN Gene Bank) originally expressing OSF-2 were plated on a 6-well plate at a density of 5×10⁵ cells/well, and the plate was incubated for 24 hours at 37° C. After 24 hours, said compounds were added at a concentration of 30 μM and cells were recovered after further 24 hours to prepare total RNA from the cells using RNeasy®Mini (QIAGEN) and the expression levels of OSF-2 mRNA and internal standard GAPDH mRNA were assayed by PCR assay system according to the method of Example 3-2 (the expression level of OSF-2 mRNA was standardized by the expression level of internal standard GAPDH mRNA). As a result, it was confirmed that 2-chloroadenosine triphosphate tetrasodium and Metrifudil inhibited the expression of OSF-2 mRNA.

Thus, it was shown that compounds influencing the expression of OSF-2 gene can be found by using the screening system shown in the present invention.

The invention claimed is:

1. An isolated nucleotide sequence consisting of SEQ ID NO: 12.

2. A pharmaceutical composition comprising an antisense nucleotide sequence comprising nucleotides complementary to 16 or more contiguous nucleotides in SEQ ID NO: 5 and a pharmacologically acceptable carrier, wherein the antisense nucleotide sequence is complementary to a nucleotide containing the initiation codon of SEQ ID NO: 5, and wherein the antisense nucleotide sequence is SEQ ID NO: 12.

3. A method of treating heart failure associated with overexpression of OSF-2 comprising, administering via injection into the heart a pharmaceutical composition comprising an effective amount of an antisense nucleotide sequence comprising nucleotides complementary to 16 or more contiguous nucleotides in SEQ ID NO: 5 to inhibit expression of OSF-2, wherein the antisense nucleotide sequence (i) does not contain three continuous guanines (triplet G), (ii) is incapable of forming a hairpin structure, and (iii) is incapable of self-annealing.

4. The method of claim 3, wherein the antisense nucleotide sequence is SEQ ID NO: 12.

5. The method of claim 3, wherein the antisense nucleotide sequence is complementary to a nucleotide containing the initiation codon of SEQ ID NO: 5.

6. The method of claim 3, further comprising determining the expression level of OSF-2 prior to administering said pharmaceutical composition.

7. A method of inhibiting OSF-2 gene expression comprising, administering via injection into the heart an effective amount of an antisense nucleotide sequence comprising nucleotides complementary to 16 or more contiguous nucleotides in SEQ ID NO: 5, whereby OSF-2 gene expression is inhibited, wherein the antisense nucleotide sequence (i) does not contain three continuous guanines (triplet G), (ii) is incapable of forming a hairpin structure, and (iii) is incapable of self-annealing.

8. The method of claim 7, wherein the antisense nucleotide sequence is SEQ ID NO: 12.

9. The method of claim 7, wherein the antisense nucleotide sequence is complementary to a nucleotide containing the initiation codon of SEQ ID NO: 5.

10. The method of claim 7, further comprising determining the expression level of OSF-2 prior to administering said antisense nucleotide sequence.

11. A method of inhibiting cardiac dilatation comprising, administering via injection into the heart a pharmaceutical composition comprising an effective amount of an antisense nucleotide sequence comprising nucleotides complementary to 16 or more contiguous nucleotides in SEQ ID NO: 5 to inhibit cardiac dilatation, wherein the antisense nucleotide sequence (i) does not contain three continuous guanines (triplet G), (ii) is incapable of forming a hairpin structure, and (iii) is incapable of self-annealing.

12. The method of claim 11, wherein the antisense nucleotide sequence is SEQ ID NO: 12.

13. The method of claim 11, wherein the antisense nucleotide sequence is complementary to a nucleotide containing the initiation codon of SEQ ID NO: 5.

14. The method of claim 11, further comprising determining the expression level of OSF-2 prior to administering said pharmaceutical composition.

* * * * *

```
                        SEQUENCE LISTING

<160> NUMBER OF SEQ ID NOS: 26

<210> SEQ ID NO 1
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 1
gttcattgaa gttggcgatg gtc                                            23

<210> SEQ ID NO 2
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 2
gagataaaat ccctgcatgg tcct                                           24

<210> SEQ ID NO 3
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 3
cacggtcgat gacatggaca acacc                                          25

<210> SEQ ID NO 4
<211> LENGTH: 22
<212> TYPE: DNA
<213> ORGANISM: Artificial Sequence
<220> FEATURE:
<223> OTHER INFORMATION: Chemicially Synthesized

<400> SEQUENCE: 4
acggagctca gggctgaaga tg                                             22

<210> SEQ ID NO 5
<211> LENGTH: 3295
<212> TYPE: DNA
<213> ORGANISM: Rattus novegicus

<400> SEQUENCE: 5
gaattccggg gatctcttcc tggacggagc tcagggctga agatggttcc tctcctgccc     60
ttatctgctc tgctgctgct gttcctgtgt gacgttgacc ccgcaaatgc caacagttac    120
tatgacaagg tcctagctca cagccgcatc aggggtcggg atcagggccc aaatgtctgt    180
gccctccagc agattctggg caccaaaaag aaatacttca gctcctgtaa gaactggtat    240
```

```
caaggtgcta tctgcgggaa gaaaaccact gtgctatatg aatgctgccc cggctatatg    300
agaatggaag ggatgaaagg ctgcccagca gtgatgccca ttgaccatgt ttatggcacg    360
ctgggcatcg tgggagccac gaccactcaa cactattctg atgtctcgaa gctcagggaa    420
gagattgaag gaaaagggtc ctacacatac ttcgcgccga gtaacgaagc ttgggacaac    480
ctggattccg acatccgcag aggactagag aacaatgtca atgttgagtt actgaacgct    540
ttacacagcc acatggttaa taagagaatg ctaaccaagg acctgaaaca cggcatggtt    600
attccttcaa tgtacaacaa tctggggctt tttatcaatc attatcccaa tggggttgtc    660
actgtgaact gtgctcgagt aatccacggg aaccagattg ccacaaatgg tgttgtccat    720
gtcatcgacc gtgtcctgac acaaattggc acctccatcc aagacttcat tgaagcagaa    780
gatgagcttt catcattcag agcggctgcc atcacttctg acctttggga gtcccttgga    840
agagacggtc acttcacact cttttgctcc accaatgagg ctttcgagaa actcccacga    900
ggagtcctag aaaggatcat gggagacaaa gtggcttctg aagctctcat gaagtaccac    960
atcctgaata ccctccagtg ctctgaggct atcacaggag gagcggtgtt tgagaccatg   1020
gaaggaaaca ctattgaaat agggtgtgag ggagacagca tctccattaa cggaatcaag   1080
atggtgaaca gaaagacat tgtgacgaag aatggtgtca tccacctgat tgatgaagtc   1140
ctcattcctg attctgctaa acaagttatt gagctggctg gaaaacagca aaccactttc   1200
acggacctgg tagcccagtt agggttggcg tcttctctga gccggatgg agagtacacg   1260 ctgttagcgc ctgtgaacaa tgcgttctct gatgacactc tgagcatgga ccagcgcctt   1320
cttaagctaa ttctgcaaaa tcacatattg aaagtaaaag tcggccttag tgatctctac   1380
aatggacaga ttctggagac cattggaggc aaacaactcc gtgtcttcgt gtatcggacg   1440
gctatctgca tagaaaactc atgcatggtg agaggaagca agcaggggag gaacggtgcc   1500
attcacatat tccgagagat catccaaccg gcggagaagt ccctgcacga aaaactgcgc   1560
caagataagc gcttcagcat cttcctcagc ctcctcgaag ctgcagatct gaaagatctt   1620
ctgacacagc ccgagattg gaccttgttt gcaccaacca atgatgcctt caagggaatg   1680
actaatgaag aaagggagat tctgattggg gataaaaatg ctctccaaaa catcattctt   1740
taccacctga ccccaggggt ttatattgga aagggatttg aacccggagt caccaacatc   1800
ctgaagacca cacagggaag caaaatctat gtgaaaggag tcaatgagac gcttttggtg   1860
aatgagttga agtccaaaga atctgacatc atgacaacaa acggcgtcat tcacgttgtg   1920
gacaaactcc tctatccagc agacattccg gttggaaatg atcagctctt ggaattactg   1980
aacaaactga taaatacat ccaaattaag ttcgttcgtg gcagcacctt caagaaaatc   2040
cccatgactg tctatacaac taaaattata accaaactcg tggaaccaaa aattaaagtc   2100
attcaaggca gtcttcagcc tattatcaaa acagaaggac ctgcaatgac gaagatccac   2160
attgaaggcg agcctgactt caggctgatt aaagaaggtg aaacagtgac agaagtgatc   2220
cacggagaac cagtcattaa aaagtacacc aaaatcatag acggggttcc tgttgaaata   2280
actgaaaaag agacccggga agaacgcatc atcacaggtc ctgagataaa atacactagg   2340
atttccacag gaggtgggga aacagaagag accctgcaga aattcttgca aaaagaggtc   2400
tccaaggtca caaagttcat tgaaggtggc gatggtcact tatttgaaga tgaggcgatt   2460
aaaagactgc ttcagggaga cacacctgca aagaagatac aagccaacaa aagggttcaa   2520
gggtctagaa ggcgatcaag agaaggccgt tctcagtgaa aattcaaagg ccagacaaca   2580
```

-continued

```
gagtttatat aatcctaaat caacaatctg attttaaggg gaaattataa gagccccatt    2640
gacttcggaa tctgaaatgg caacaaacag aagctaattg tcaagcaaat ctgaacgcag    2700
agttaatttg tttctgaatg agaaacatag gaaaatgata gtctcctgtg gggtaggaac    2760
tgaaggaaat ataggaccat gcagggattt tatctcaatg agagaagttc tgattatatt    2820
aggaatccac caaagaccat cattgtgact ggatccacac agctaagtct ttgctcagtg    2880
aacatggtca agaagaggct ggaaaaaccc aaagcacaca gttacctttc catgggaggc    2940
taagctatca aaagcggtgt tcagttatac aacaagcaag ccaagccacc aaattacaaa    3000
cagtggtgtt acatatttct cgtgcaatgt gggtttcctg ctaaattttg ttgttttttac   3060 acttgattta tatcctcgag atgattgtca tatgcttttt gcagtacaaa tgtttctctc    3120
aaacatttca ataaaaacat tcttcaggta taaagagaat tacttcagac ttggtaattc    3180
agaaaactca aggtttaagt taaagtgag tttagacttt ggaataggac ttcatacctt     3240
tttttattgt taacaagtac tcaataaagg aatctgaata aaaaaaacgg aattc         3295
```

<210> SEQ ID NO 6
<211> LENGTH: 838
<212> TYPE: PRT
<213> ORGANISM: Rattus norvegicus

<400> SEQUENCE: 6

```
Met Val Pro Leu Leu Pro Leu Ser Ala Leu Leu Leu Phe Leu Cys
1               5                   10                  15

Asp Val Asp Pro Ala Asn Ala Asn Ser Tyr Tyr Asp Lys Val Leu Ala
            20                  25                  30

His Ser Arg Ile Arg Gly Arg Asp Gln Gly Pro Asn Val Cys Ala Leu
        35                  40                  45

Gln Gln Ile Leu Gly Thr Lys Lys Lys Tyr Phe Ser Ser Cys Lys Asn
    50                  55                  60

Trp Tyr Gln Gly Ala Ile Cys Gly Lys Lys Thr Val Leu Tyr Glu
65                  70                  75                  80

Cys Cys Pro Gly Tyr Met Arg Met Glu Gly Met Lys Gly Cys Pro Ala
                85                  90                  95

Val Met Pro Ile Asp His Val Tyr Gly Thr Leu Gly Ile Val Gly Ala
            100                 105                 110

Thr Thr Thr Gln His Tyr Ser Asp Val Ser Lys Leu Arg Glu Glu Ile
        115                 120                 125

Glu Gly Lys Gly Ser Tyr Thr Tyr Phe Ala Pro Ser Asn Glu Ala Trp
    130                 135                 140

Asp Asn Leu Asp Ser Asp Ile Arg Arg Gly Leu Glu Asn Asn Val Asn
145                 150                 155                 160

Val Glu Leu Leu Asn Ala Leu His Ser His Met Val Asn Lys Arg Met
                165                 170                 175

Leu Thr Lys Asp Leu Lys His Gly Met Val Ile Pro Ser Met Tyr Asn
            180                 185                 190

Asn Leu Gly Leu Phe Ile Asn His Tyr Pro Asn Gly Val Val Thr Val
        195                 200                 205

Asn Cys Ala Arg Val Ile His Gly Asn Gln Ile Ala Thr Asn Gly Val
    210                 215                 220

Val His Val Ile Asp Arg Val Leu Thr Gln Ile Gly Thr Ser Ile Gln
225                 230                 235                 240

Asp Phe Ile Glu Ala Glu Asp Glu Leu Ser Ser Phe Arg Ala Ala Ala
                245                 250                 255
```

-continued

```
Ile Thr Ser Asp Leu Leu Glu Ser Leu Gly Arg Asp Gly His Phe Thr
        260                 265                 270
Leu Phe Ala Pro Thr Asn Glu Ala Phe Glu Lys Leu Pro Arg Gly Val
        275                 280                 285
Leu Glu Arg Ile Met Gly Asp Lys Val Ala Ser Glu Ala Leu Met Lys
        290                 295                 300
Tyr His Ile Leu Asn Thr Leu Gln Cys Ser Glu Ala Ile Thr Gly Gly
305                 310                 315                 320
Ala Val Phe Glu Thr Met Glu Gly Asn Thr Ile Glu Ile Gly Cys Glu
                325                 330                 335
Gly Asp Ser Ile Ser Ile Asn Gly Ile Lys Met Val Asn Lys Lys Asp
                340                 345                 350
Ile Val Thr Lys Asn Gly Val Ile His Leu Ile Asp Glu Val Leu Ile
                355                 360                 365
Pro Asp Ser Ala Lys Gln Val Ile Glu Leu Ala Gly Lys Gln Gln Thr
        370                 375                 380
Thr Phe Thr Asp Leu Val Ala Gln Leu Gly Leu Ala Ser Ser Leu Lys
385                 390                 395                 400
Pro Asp Gly Glu Tyr Thr Leu Leu Ala Pro Val Asn Asn Ala Phe Ser
                405                 410                 415
Asp Asp Thr Leu Ser Met Asp Gln Arg Leu Leu Lys Leu Ile Leu Gln
                420                 425                 430
Asn His Ile Leu Lys Val Lys Val Gly Leu Ser Asp Leu Tyr Asn Gly
                435                 440                 445
Gln Ile Leu Glu Thr Ile Gly Gly Lys Gln Leu Arg Val Phe Val Tyr
        450                 455                 460
Arg Thr Ala Ile Cys Ile Glu Asn Ser Cys Met Val Arg Gly Ser Lys
465                 470                 475                 480
Gln Gly Arg Asn Gly Ala Ile His Ile Phe Arg Glu Ile Ile Gln Pro
                485                 490                 495
Ala Glu Lys Ser Leu His Glu Lys Leu Arg Gln Asp Lys Arg Phe Ser
                500                 505                 510
Ile Phe Leu Ser Leu Leu Glu Ala Ala Asp Leu Lys Asp Leu Leu Thr
        515                 520                 525
Gln Pro Gly Asp Trp Thr Leu Phe Ala Pro Thr Asn Asp Ala Phe Lys
        530                 535                 540
Gly Met Thr Asn Glu Glu Arg Glu Ile Leu Ile Gly Asp Lys Asn Ala
545                 550                 555                 560
Leu Gln Asn Ile Ile Leu Tyr His Leu Thr Pro Gly Val Tyr Ile Gly
                565                 570                 575
Lys Gly Phe Glu Pro Gly Val Thr Asn Ile Leu Lys Thr Thr Gln Gly
                580                 585                 590
Ser Lys Ile Tyr Val Lys Gly Val Asn Glu Thr Leu Leu Val Asn Glu
                595                 600                 605
Leu Lys Ser Lys Glu Ser Asp Ile Met Thr Thr Asn Gly Val Ile His
        610                 615                 620
Val Val Asp Lys Leu Leu Tyr Pro Ala Asp Ile Pro Val Gly Asn Asp
625                 630                 635                 640
Gln Leu Leu Glu Leu Asn Lys Leu Ile Lys Tyr Ile Gln Ile Lys
                645                 650                 655
Phe Val Arg Gly Ser Thr Phe Lys Glu Ile Pro Met Thr Val Tyr Thr
                660                 665                 670
```

-continued

```
Thr Lys Ile Ile Thr Lys Leu Val Glu Pro Lys Ile Lys Val Ile Gln
        675                 680                 685

Gly Ser Leu Gln Pro Ile Ile Lys Thr Glu Gly Pro Ala Met Thr Lys
        690                 695                 700

Ile His Ile Glu Gly Glu Pro Asp Phe Arg Leu Ile Lys Glu Gly Glu
705                 710                 715                 720

Thr Val Thr Glu Val Ile His Gly Glu Pro Val Ile Lys Lys Tyr Thr
                725                 730                 735

Lys Ile Ile Asp Gly Val Pro Val Glu Ile Thr Glu Lys Glu Thr Arg
                740                 745                 750

Glu Glu Arg Ile Ile Thr Gly Pro Glu Ile Lys Tyr Thr Arg Ile Ser
            755                 760                 765

Thr Gly Gly Gly Glu Thr Glu Glu Thr Leu Gln Lys Phe Leu Gln Lys
        770                 775                 780

Glu Val Ser Lys Val Thr Lys Phe Ile Glu Gly Gly Asp Gly His Leu
785                 790                 795                 800

Phe Glu Asp Glu Ala Ile Lys Arg Leu Leu Gln Gly Asp Thr Pro Ala
                805                 810                 815

Lys Lys Ile Gln Ala Asn Lys Arg Val Gln Gly Ser Arg Arg Arg Ser
                820                 825                 830

Arg Glu Gly Arg Ser Gln
        835

<210> SEQ ID NO 7
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 7
tgcaaaaaga ggtctccaag gt                                          22

<210> SEQ ID NO 8
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 8
aggtgtgtct ccctgaagca gt                                          22

<210> SEQ ID NO 9
<211> LENGTH: 28
<212> TYPE: DNA
<213> ORGANISM: Artificial Sequence
<220> FEATURE:
<223> OTHER INFORMATION: Chemically Synthesized

<400> SEQUENCE: 9
acaaagttca ttgaaggtgg cgatggtc                                    28

<210> SEQ ID NO 10
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 10
```

| | |
|---|---|
| gacccgggaa gaacgcatca tc | 22 |

<210> SEQ ID NO 11
<211> LENGTH: 32
<212> TYPE: DNA
<213> ORGANISM: Artificial Sequence
<220> FEATURE:
<223> OTHER INFORMATION: Chemically Synthesized

<400> SEQUENCE: 11

| | |
|---|---|
| tgggtgaccc tgagaacggc cttctcttga tc | 32 |

<210> SEQ ID NO 12
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 12

| | |
|---|---|
| aggaaccatc ttcagccctg | 20 |

<210> SEQ ID NO 13
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 13

| | |
|---|---|
| gagaggaacc atcttcagcc | 20 |

<210> SEQ ID NO 14
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 14

| | |
|---|---|
| aggagaggaa ccatcttcag | 20 |

<210> SEQ ID NO 15
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 15

| | |
|---|---|
| gcaggagagg aaccatcttc | 20 |

<210> SEQ ID NO 16
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 16

| | |
|---|---|
| agggcaggag aggaaccatc | 20 |

<210> SEQ ID NO 17
<211> LENGTH: 20
<212> TYPE: DNA
<213> ORGANISM: Artificial Sequence

```
<220> FEATURE:
<223> OTHER INFORMATION: Chemically Synthesized

<400> SEQUENCE: 17
cagggctgaa gatggttcct                                                      20

<210> SEQ ID NO 18
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 18
gtcccgactt ctaccaagga                                                      20

<210> SEQ ID NO 19
<211> LENGTH: 3215
<212> TYPE: DNA
<213> ORGANISM: Mus musculus

<400> SEQUENCE: 19
gaattcgcgg ccgccggagc tcagggctga agatggttcc tctcctgccc ttatatgctc        60
tgctgctgct gttcctgtgt gatattaacc ctgcaaatgc caacagttac tatgacaagg       120
tcctggctca cagccgcatc aggggtcggg atcagggccc aaacgtctgt gccctccagc       180
aaattctggg caccaaaaag aaatacttca gctcctgtaa aactggtat caaggtgcta        240 tctgcgggaa gaaaaccact gtgctatatg aatgctgccc tggctatatg agaatggaag       300
ggatgaaagg ctgccccgca gtgatgccta ttgaccatgt ttatggcacg ctgggcattg       360
tgggagccac taccactcag cactactccg atgtctcgaa gctgagagaa gagattgaag       420
gaaaagggtc atacacgtac ttcgcgccga gtaacgaggc ttgggagaac ctggattctg       480
acattcgcag aggactggag aacaatgtca atgttgagct actgaatgcc ttacacagcc       540
acatggttaa taagagaatg ttaaccaagg acctgaaaca cggcatggtt attccttcaa       600
tgtacaacaa tctggggctt tttattaacc attatcccaa tgggttgtc actgtgaact         660 gtgctcgagt catccatggg aaccagattg ccacaaatgg tgtcgtccat gtcattgacc       720
gtgtcctgac acaaattggt acctccatcc aagacttcct tgaagcagaa gacgaccttt       780
catcatttag agcagccgcc atcacctctg acctcttgga gtcccttgga agagatggtc       840
acttcacgct ctttgctccc accaatgaag ctttcgagaa actgccacga ggtgtcctag       900
aaaggatcat gggagacaaa gtggcttctg aagctctcat gaagtaccac atcctaaata       960
ccctccagtg ctctgaggcc atcactggag gagccgtgtt tgagaccatg aaggaaaca      1020 ctattgagat agggtgcgaa ggggacagta tctccattaa cggaatcaag atggtgaaca       1080
agaaagacat tgtgactaag aatggtgtca tccacctgat tgatgaagtc ctcattcctg       1140
attctgccaa acaagttatt gagctggctg aaaacagca aaccactttc accgacctgg       1200
tagcccaatt aggcttggca tcctctctga agccagatgg agagtacacc ttattagcac       1260
ctgtgaacaa tgcgttctct gatgacactc tgagcatgga ccaacgcctt cttaagctaa       1320
ttctgcaaaa tcacatattg aaagtaaaag ttggccttag cgacctctac aatggacaga       1380
tactggaaac cattggaggc aaacaactcc gagtctttgt gtatcggacg ctatctgca        1440 tagaaaactc atgcatggtg agaggaagca agcaggaag gaatggtgcc attcacatat        1500
tccgagaaat catccaacca gcagagaaat ccctgcacga caagctgcgg caagacaagc      1560
```

-continued

```
gctttagcat cttcctcagc ctccttgaag ctgcagattt gaaagatctc ctgacacagc      1620
ccggagattg gaccttgttt gcaccaacca atgatgcctt caagggaatg actagcgaag      1680
aaagggagct tctgattggg gataaaaatg ctctccaaaa catcattctt tatcacctga      1740 ccccagggt ttatattgga aagggattcg aacccggagt cactaatatc ctgaagacca       1800 cacaggaag caaaatctat ctgaaggag taaacgaaac gcttctagtg aatgagttga        1860
agtccaaaga atctgacatc atgacgacaa atggtgtcat ccacgtcgtg acaaactcc       1920 tctatccagc agatattcca gttggaaatg atcagctctt ggaattactg aacaaactga     1980
taaaatacat ccaaatcaag tttgttcgtg gcagcacctt caaagaaatc ccatgactg       2040 tctatagacc tgcaatgacg aagatccaaa ttgaaggtga tcccgacttc aggctgatta     2100
aagaaggcga acggtgaca gaagtgatcc acggagagcc agtcattaaa aagtacacca      2160
aaatcataga tggagttcct gttgaaataa ctgaaaaaca gactcgggaa gaacgaatca    2220
ttacaggtcc tgagataaaa ataccagga tttccacagg aggtgagaa acaggagaga      2280 ccttgcagaa attcttgcaa aaagaggtct ccaaggtcac aaagttcatt gaaggtggcg     2340
atggtcactt atttgaagat gaggagatta aagactgct tcaggagac acacctgcaa       2400 agaagatacc agccaacaaa agggttcaag ggcctagaag acgatcaaga gaaggccgtt    2460
ctcagtgaaa acccagaggc cagaccacag agtttatata atcctaaatc aacgatctga   2520
ttttaaggga aattgtaaga gccaccacac tgacttcaga atctgaaatg caaccaaca    2580 gaagccaatt cccaagcaag tccaaacaca gagttcatgt ctttgtttct gcatgagaaa    2640
tataagaaaa tgatagctag tctcctgtgg ggtaggaact gaggaaatat aggaccatgc     2700 agggattta tctcaatgag aaaacttctg attaaagtag aatccaccaa agaacatcat      2760
tgtgactggg tccatacagc taagtctttg cacagtaaaa accttccgcc tcaggaagag    2820 gctgaaaaa cccaaagcac acagttacct ttccagggga ggctaaggta tcaaaagggg     2880
tgttcagtta tacaacatgc aaacaaacct accaaattac gaacagtggt gttacatatt     2940
tctcatgcaa tgtgggtttc ctgctaaatt ttgttatttt tacacttgat ttatatcctc    3000
gagatgattg tcataagctt cttgcaatac aaatgttttc tctcaaacat ttcaataaaa    3060
ccattcttca ggtataaaga gaattactgc agagttggta attcagaaaa ctcaaggttt    3120
aagttaaaag tgagtttaga cttggaata ggacttcata cctttttta ttgttaacaa      3180 gtactcaata aagtaaactg agcggccgcg aattc                                3215
```

<210> SEQ ID NO 20
<211> LENGTH: 3092
<212> TYPE: DNA
<213> ORGANISM: Homo sapiens

<400> SEQUENCE: 20

```
gaattcgggg aacagaactg caacggagag actcaagatg attcccttt tacccatgtt       60 ttctctacta ttgctgctta ttgttaaccc tataaacgcc aacaatcatt atgacaagat      120
cttggctcat agtcgtatca ggggtcggga ccaaggccca atgtctgtg cccttcaaca       180 gattttgggc accaaaaaga aatacttcag cacttgtaag aactggtata aaaagtccat      240
ctgtggacag aaaacgactg ttttatatga atgttgccct ggttatatga gaatggaagg     300
aatgaaaggc tgcccagcag ttttgcccat tgaccatgtt tatggcactc tgggcatcgt    360
gggagccacc acaacgcagc gctattctga cgcctcaaaa ctgagggagg agatcgaggg    420
aaagggatcc ttcacttact ttgcaccgag taatgaggct tgggacaact tggattctga   480
```

-continued

| | |
|---|---|
| tatccgtaga ggtttggaga gcaacgtgaa tgttgaatta ctgaatgctt tacatagtca | 540 |
| catgattaat aagagaatgt tgaccaagga cttaaaaaat ggcatgatta ttccttcaat | 600 |
| gtataacaat ttggggcttt tcattaacca ttatcctaat ggggttgtca ctgttaattg | 660 |
| tgctcgaatc atccatggga accagattgc aacaaatggt gttgtccatg tcattgaccg | 720 |
| tgtgcttaca caaattggta cctcaattca agacttcatt gaagcagaag atgacctttc | 780 |
| atcttttaga gcagctgcca tcacatcgga catattggag gcccttggaa gagacggtca | 840 |
| cttcacactc tttgctccca ccaatgaggc ttttgagaaa cttccacgag gtgtcctaga | 900 |
| aaggttcatg ggagacaaag tggcttccga agctcttatg aagtaccaca tcttaaatac | 960 |
| tctccagtgt tctgagtcta ttatggggag agcagtcttt gagacgctgg aaggaaatac | 1020 |
| aattgagata ggatgtgacg gtgacagtat aacagtaaat ggaatcaaaa tggtgaacaa | 1080 |
| aaaggatatt gtgacaaata atggtgtgat ccatttgatt gatcaggtcc taattcctga | 1140 |
| ttctgccaaa caagttattg agctggctgg aaaacagcaa accaccttca cggatcttgt | 1200 |
| ggcccaatta ggcttggcat ctgctctgag gccagatgga gaatacactt tgctggcacc | 1260 |
| tgtgaataat gcattttctg atgatactct cagcatggtt cagcgcctcc ttaaattaat | 1320 |
| tctgcagaat cacatattga agtaaaagt tggccttaat gagctttaca acggcaaat | 1380 |
| actgaaaacc atcggaggca acagctcag agtcttcgta tatcgtacag ctgtctgcat | 1440 |
| tgaaaattca tgcatggaga aagggagtaa gcaagggaga acggtgcga ttcacatatt | 1500 |
| ccgcgagatc atcaagccag cagagaaatc cctccatgaa aagttaaaac aagataagcg | 1560 |
| ctttagcacc ttcctcagcc tacttgaagc tgcagacttg aaagagctcc tgacacaacc | 1620 |
| tggagactgg acattatttg tgccaaccaa tgatgcttt aagggaatga ctagtgaaga | 1680 |
| aaaagaaatt ctgatacggg acaaaaatgc tcttcaaaac atcattcttt atcacctgac | 1740 |
| accaggagtt ttcattggaa aaggatttga acctggtgtt actaacattt taaagaccac | 1800 |
| acaaggaagc aaaatctttc tgaaagaagt aaatgataca cttctggtga atgaattgaa | 1860 |
| atcaaaagaa tctgacatca tgacaacaaa tggtgtaatt catgttgtag ataaactcct | 1920 |
| ctatccagca gacacacctg ttggaaatga tcaactgctg gaaatactta ataaattaat | 1980 |
| caaatacatc caaattaagt tgttcgtgg tagcaccttc aaagaaatcc ccgtgactgt | 2040 |
| ctataagcca attattaaaa atacaccaa atcattgat ggagtgcctg tggaaataac | 2100 |
| tgaaaaagag acacgagaag aacgaatcat tacaggtcct gaaataaaat acactaggat | 2160 |
| ttctactgga ggtggagaaa cagaagaaac tctgaagaaa ttgttacaag aagaggtcac | 2220 |
| caaggtcacc aaattcattg aaggtggtga tggtcattta tttgaagatg aagaaattaa | 2280 |
| aagactgctt cagggagaca cacccgtgag gaagttgcaa gccaacaaaa agttcaagg | 2340 |
| ttctagaaga cgattaaggg aaggtcgttc tcagtgaaaa tccaaaaacc agaaaaaaat | 2400 |
| gtttatacaa ccctaagtca ataacctgac cttagaaaat tgtgagagcc aagttgactt | 2460 |
| caggaactga aacatcagca caagaagca atcatcaaat aattctgaac acaaatttaa | 2520 |
| tatttttttt tctgaatgag aaacatgagg gaaattgtgg agttagcctc ctgtggagtt | 2580 |
| agcctcctgt ggtaaaggaa ttgaagaaaa tataacacct tacacccttt ttcatcttga | 2640 |
| cattaaaagt tctggctaac tttggaatcc attagagaaa aatccttgtc accagattca | 2700 |
| ttacaattca aatcgaagag ttgtgaactg ttatcccatt gaaagaccg agccttgtat | 2760 |
| gtatgttatg gatacataaa atgcacgcaa gccattatct ctccatggga agctaagtta | 2820 |

-continued

| | |
|---|---|
| taaaaatagg tgcttggtgt acaaaacttt ttatatcaaa aggctttgca catttctata | 2880 |
| tgagtgggtt tactggtaaa ttatgttatt tttaatcact aattttgtac tctcagaatg | 2940 |
| tttgtcatat gcttcttgca atgcatattt ttttatctca aacgtttcaa taaaaccatt | 3000 |
| tttcagatat aaagagaatt acttcaaatt gagtaattca gaaaaactca agatttaagt | 3060 |
| taaaaagtgg tttggacttg ggaacaggac tt | 3092 |

<210> SEQ ID NO 21
<211> LENGTH: 3253
<212> TYPE: DNA
<213> ORGANISM: Homo sapien

<400> SEQUENCE: 21

| | |
|---|---|
| gaattcggag atctacaggg agagactcaa gatgattccc tttttaccca tgttttctct | 60 |
| actattgctg cttattgtta accctataaa cgccaacaat cattatgaca agatcttggc | 120 |
| tcatagtcgt atcaggggtc gggaccaagg cccaaatgtc tgtgcccttc aacagatttt | 180 |
| gggcaccaaa aagaaatact tcagcacttg taagaactgg tataaaaagt ccatctgtgg | 240 |
| acagaaaacg actgttttat atgaatgttg ccctggttat atgagaatgg aaggaatgaa | 300 |
| aggctgccca gcagttttgc ccattgacca tgtttatggc actctgggca tcgtgggagc | 360 |
| caccacaacg cagcgctatt ctgacgcctc aaaactgagg gaggagatcg agggaaaggg | 420 |
| atccttcact tactttgcac cgagtaatga ggcttgggac aacttggatt ctgatatccg | 480 |
| tagaggtttg gagagcaacg tgaatgttga attactgaat gctttacata gtcacatgat | 540 |
| taataagaga atgttgacca aggacttaaa aaatggcatg attattcctt caatgtataa | 600 |
| caatttgggg cttttcatta accattatcc taatgggggtt gtcactgtta attgtgctcg | 660 |
| aatcatccat gggaaccaga ttgcaacaaa tggtgttgtc catgtcattg accgtgtgct | 720 |
| tacacaaatt ggtacctcaa ttcaagactt cattgaagca gaagatgacc tttcatcttt | 780 |
| tagagcagct gccatcacat cggacatatt ggaggccctt ggaagagacg gtcacttcac | 840 |
| actctttgct cccaccaatg aggcttttga gaaacttcca cgaggtgtcc tagaaaggtt | 900 |
| catgggagac aaagtggctt ccgaagctct tatgaagtac cacatcttaa atactctcca | 960 |
| gtgttctgag tctattatgg gaggagcagt ctttgagacg ctggaaggaa atacaattga | 1020 |
| gataggatgt gacggtgaca gtataacagt aaatggaatc aaaatggtga acaaaaagga | 1080 |
| tattgtgaca ataatggtg tgatccattt gattgatcag gtcctaattc ctgattctgc | 1140 |
| caaacaagtt attgagctgg ctggaaaaca gcaaaccacc ttcacggatc ttgtggccca | 1200 |
| attaggcttg gcatctgctc tgaggccaga tggagaatac actttgctgg cacctgtgaa | 1260 |
| taatgcattt tctgatgata ctctcagcat ggttcagcgc ctccttaaat taattctgca | 1320 |
| gaatcacata ttgaaagtaa aagttggcct taatgagctt tacaacgggc aaatactgga | 1380 |
| aaccatcgga ggcaaacagc tcagagtctt cgtatatcgt acagctgtct gcattgaaaa | 1440 |
| ttcatgcatg gagaaaggga gtaagcaagg gagaaacggt gcgattcaca tattccgcga | 1500 |
| gatcatcaag ccagcagaga atccctcca tgaaaagtta aaacaagata gcgctttag | 1560 |
| caccttcctc agcctacttg aagctgcaga cttgaaagag ctcctgacac aacctggaga | 1620 |
| ctggacatta tttgtgccaa ccaatgatgc ttttaaggga atgactagtg aagaaaaaga | 1680 |
| aattctgata cgggacaaaa atgctcttca aaacatcatt ctttatcacc tgacaccagg | 1740 |
| agttttcatt ggaaaaggat ttgaacctgg tgttactaac attttaaaga ccacacaagg | 1800 |
| aagcaaaatc tttctgaaag aagtaaatga tacacttctg gtgaatgaat tgaaatcaaa | 1860 |

-continued

```
agaatctgac atcatgacaa caaatggtgt aattcatgtt gtagataaac tcctctatcc    1920
agcagacaca cctgttggaa atgatcaact gctggaaata cttaataaat taatcaaata    1980
catccaaatt aagtttgttc gtggtagcac cttcaaagaa atccccgtga ctgtctatac    2040
aactaaaatt ataaccaaag ttgtggaacc aaaaattaaa gtgattgaag gcagtcttca    2100
gcctattatc aaaactgaag gacccacact aacaaaagtc aaaattgaag gtgaacctga    2160
attcagactg attaaagaag gtgaaacaat aactgaagtg atccatggag agccaattat    2220
taaaaaatac accaaaatca ttgatggagt gcctgtggaa ataactgaaa agagacacg     2280 agaagaacga atcattacag gtcctgaaat aaaatacact aggatttcta ctggaggtgg    2340
agaaacagaa gaaactctga agaaattgtt acaagaagag gtcaccaagg tcaccaaatt    2400
cattgaaggt ggtgatggtc atttatttga agatgaagaa attaaaagac tgcttcaggg    2460
agacacaccc gtgaggaagt tgcaagccaa caaaaaagtt caaggttcta gaagacgatt    2520
aagggaaggt cgttctcagt gaaatccaa aaccagaaa aaaatgttta tacaacccta     2580
agtcaataac ctgaccttag aaaattgtga gagccaagtt gacttcagga actgaaacat    2640
cagcacaaag aagcaatcat caaataattc tgaacacaaa tttaatattt tttttctga    2700 atgagaaaca tgagggaaat tgtggagtta gcctcctgtg gtaaaggaat tgaagaaaat    2760 ataacaccctt acacccttttt tcatcttgac attaaaagtt ctggctaact ttggaatcca   2820
ttagagaaaa atccttgtca ccagattcat tacaattcaa atcgaagagt tgtgaactgt    2880
tatcccattg aaaagaccga gccttgtatg tatgttatgg atacataaaa tgcacgcaag    2940
ccattatctc tccatgggaa gctaagttat aaaaataggt gcttggtgta caaaacttt    3000 tatatcaaaa ggctttgcac atttctatat gagtgggttt actggtaaat tatgttattt    3060
tttacaacta attttgtact ctcagaatgt ttgtcatatg cttcttgcaa tgcatatttt    3120
ttaatctcaa acgtttcaat aaaaccattt ttcagatata aagagaatta cttcaaattg    3180
agtaattcag aaaaactcaa gatttaagtt aaaaagtggt ttggacttgg gaaccctgta    3240
gatctccgaa ttc                                                      3253

<210> SEQ ID NO 22
<211> LENGTH: 38
<212> TYPE: DNA
<213> ORGANISM: Artificial Sequence
<220> FEATURE:
<223> OTHER INFORMATION: Chemically Synthesized

<400> SEQUENCE: 22
aagaatatta aaagttattt gtgggcagga gacagatg                            38

<210> SEQ ID NO 23
<211> LENGTH: 35
<212> TYPE: DNA
<213> ORGANISM: Artificial Sequence
<220> FEATURE:
<223> OTHER INFORMATION: Chemically Synthesized

<400> SEQUENCE: 23
catttaaaag cctatcaagt gtcaggtcca ctctc                               35

<210> SEQ ID NO 24
<211> LENGTH: 2141
<212> TYPE: DNA
<213> ORGANISM: Homo sapien
```

<400> SEQUENCE: 24

```
actagtgcat aaaactggtt gcaaagaacg actaggttaa aattgttctt gaaaataatc        60
aataaaattt taattcgttc caggcaatat taagaaagca ggcaacatgg caggaaattt       120
tgattcttcc ttcactcctt gtattcacaa tcaggtctat cagttatcat tccggactgt       180
atttaaaaat atatatttttt ttacccttga tacttattac acaagtctat atctctttct      240
ctgagtacct catccttcac ctccagtcaa accctattgg atttgagcag atatcagctt       300
cattacaaaa aggtctgtaa gtagttacat cagtctaaag atgaaaagtg tggcattagt       360
agcagtgtaa tctatattat aatgtctaac tggtctagag ttgaagactt ttatatatcc       420
atttaaccag gaatgtccta acagctaatt taataatatt gatagtttat ccgtcctaat       480
caataagcag ttactgacca cctgccattt gcacaacata agagtaatag aaagctataa       540
tataaagcaa aagatgactt cataaagtca gaatgattcc attcagagaa atgtaaatga       600
tagactaaac tcttccttcc acaaaggacc agggtcagaa tataatttaa cttttatgct       660
atctcctctc cagctcttct tttgaattgc cccttcattt tctataactt aatcccaaga       720
ttttcatatt gaaatggcct ctcgatcata tttcagcatt tgttgtttca ctgtgtgctt       780
tcttaataaa ctaagcagca agttgtagaa tattttaata tcccatagtg agtttaagca       840
taactcagga tactcagaat cctctctagt tcagtccagt tcccctaaag ccttcccaat       900
agaacaacaa ggagaattct gacaaaatct ctctatctca ccagtgggaa aagaacatgg       960
atatgacatt acagagggag catcttgtag caaaatggat tggaattaca ctttaggatg      1020
gtgtgcagct tgtttattca aggaagctga ttgtggttac catttcagct cattgtttcc      1080
ctctgatatt cagatttcct ttatccaaag ttttctgaac atttgacata tgcatggagt      1140
agtaagaacg cacattcctt tggctaggga ttgcatagtg taacattgaa aggctttagt      1200
tattcttgat aaaatcagaa gaatcatttt ggcaatgtcc atgtttccta atatgtatt       1260
aattgttcta gttatctcta gattcgtaac acttgcttcc aatattggct gcttttcacc      1320
agtggttatc agtagatgtg ctgcatagac atgttcaaca tcacataaag tgtgtcatga      1380
aaaacaataa agcacaaatg ttttttccttt ctgcttcatt tcaaaccttt gagaaatttg      1440
tcagagtaga tttatgttaa ctctatatgt tccttgatat ttgaaaaaga aggaaatga       1500
gaggtagctc tcctttttgt acgatagcaa ggaaaatatg gactctccta catggttctt      1560
cagcaagtta gaattcttat ttcatatctt acacaagttt taaatctatc cagagtttgt      1620
ttttaatcaa cagcctttac ccccttgtga ttgtcagact cgcatctacc tttgttttct      1680
ggtaaaaata ataataataa taatctttca gttctgatgt gaactgcaat aacacctaac      1740
aataatcttg agcacacaga cattatacat tctactctgg aaaggattgc agaatatctc      1800
ttaaaactca acaaaagaat ttttcttaaa aaccctctaa gatacaaagg aataaaactg      1860
agacttaaac atgcagtgag tcaattgttc atatgattaa aaataagtac cttctttata      1920
atgaaaagga aaagtagctc aatgtgttcc ttaaatataa ctaaccaaaa caaatcttag      1980
ctggcaattt gaagttgccg atgcttcctg gaaagagttc agactctcag gttgatgcag      2040
tgttccctcc cacaactctg acatgtatat aaattctgag ctctccaaag cccactgcca      2100
gttctgttcg ggactaact gcaacggaga gactcaagat g                           2141
```

<210> SEQ ID NO 25
<211> LENGTH: 20
<212> TYPE: DNA
<213> ORGANISM: Artificial Sequence

```
<220> FEATURE:
<223> OTHER INFORMATION: Chemically Synthesized

<400> SEQUENCE: 25
tgagcatata tcatgctttc                                              20

<210> SEQ ID NO 26
<211> LENGTH: 35
<212> TYPE: DNA
<213> ORGANISM: Artificial Sequence
<220> FEATURE:
<223> OTHER INFORMATION: Chemically Synthesized

<400> SEQUENCE: 26
aatcatctcg agtctctccg ttgcagttag tcccc                             35
```